United States Patent
Bhardwaj et al.

(10) Patent No.: US 7,888,088 B2
(45) Date of Patent: Feb. 15, 2011

(54) SUPEROXIDE DISMUTASE (SOD) GENE AND A METHOD OF IDENTIFYING AND CLONING THEREOF

(75) Inventors: Pardeep Kumar Bhardwaj, Palampur (IN); Rashita Sahoo, Palampur (IN); Sanjay Kumar, Palampur (IN); Paramvir Singh Ahuja, Palampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 189 days.

(21) Appl. No.: 12/315,301

(22) Filed: Dec. 2, 2008

(65) Prior Publication Data

US 2010/0261268 A1    Oct. 14, 2010

Related U.S. Application Data

(62) Division of application No. 11/499,505, filed on Aug. 4, 2006, now abandoned.

(30) Foreign Application Priority Data

Mar. 31, 2006    (IN) .......................... 928/DEL/2006

(51) Int. Cl.
| | |
|---|---|
| C12N 9/02 | (2006.01) |
| C12N 1/20 | (2006.01) |
| C12N 15/00 | (2006.01) |
| C12Q 1/68 | (2006.01) |
| C07H 21/04 | (2006.01) |
| C07H 21/02 | (2006.01) |

(52) U.S. Cl. .................... 435/189; 435/6; 435/252.3; 435/320.1; 536/23.1; 536/23.2

(58) Field of Classification Search .................... None
See application file for complete search history.

(56) References Cited

U.S. PATENT DOCUMENTS 6,485,950 B1    11/2002   Kumar et al.
7,037,697 B2    5/2006    Kumar et al.

*Primary Examiner*—Yong D Pak
(74) *Attorney, Agent, or Firm*—Edwards Angell Palmer & Dodge LLP; Jeffrey D. Hsi; Elizabeth Spar

(57) ABSTRACT

The present invention provides a superoxide dismutase gene from *Potentilla atrosanguinea*, a construct containing the gene coding for superoxide dismutase and transformed *E. coli* producing the SOD protein.

5 Claims, 28 Drawing Sheets

Fig. 2. Comparison of the nucleotide sequence of the *Potentilla* Cu/Zn SOD with sequences from other plant species. Regions of complete homology are indicated with asterisks.

```
Malus        ATGGTGAAGGGTGTTGCTGTTCTCGGCTCCAGTGAGGGCGTTAAAGGAACCATCAGCTTT
Potentilla   ATGGCAAAGGGCGTTGCTGTACTTAGCTCCAGTGAGGGTGTTGCTGGAACTATCCTCTTT
Populus      ATGGTGAAGGCTGTAGCTGTTCTTAATAGCAGTGAAGGTGTGAGTGGCACCATCTTCTTT
Pea          ATGGTGAAGGCTGTGGCAGTTCTTAGTAACAGTAACGAAGTCTCGGGTACTATTAACTTC
Arabidopsis  ATGGCGAAAGGAGTTGCAGTTTTTGAACAGCAGTGAGGGTGTTACGGGGACTATCTTTTTC
Oryza        ATGGTGAAGGCTGTTGCTGTGCTTGCTAGCAGTGAGGGTGTCAAGGGCACCATCTTTTTC
             ****  ** *  ** ** **  *     **** * *  **    ** ** **     **

Malus        GTCCAGGAGGGAGATGGCCCAACTACTGTGACTGGAAGTGTCTCTGGCCTCAAGCCTGGA
Potentilla   ACCCAACACCCAGATCGCCCAACTACTCTCACCCCAAACATTTCTCCCCTCAAGCCTCCC
Populus      ACCCAAGAAGGAGATGGCCCAACTACTGTAATTGGAAACCTTTCTGGTCTTAAGCCAGGC
Pea          ACTCAGCAGCCAAATCGTCCAACCACTGTAACTGCAACTCTTGCTGCTCTTAACCCTCCC
Arabidopsis  ACCCAGGAAGGCGATGGTGTGACCACTGTGAGTGGAACAGTTTCTGGCCTTAAGCCTGGT
Oryza        TCCCAAGAGGGAGATGGTCCGACCTCTGTGACGGGAAGTGTCTCTGGGCTCAAGCCAGGG
                ** ** **   ****        **  **** *  ****   * **** ** ***** **

Malus        CTTCATGGTTTCCATGTCCATGCTCTTGGAGACACAACAAACGGTTGCATGTCAACTGGG
Potentilla   CTTCATGGTTTCCATGTTCATGCTCTTGGGGACACAACCAATGGTTGCATGTCAACTGGA
Populus      CTTCATGGCTTCCACGTCCATGCCCTTGGAGACACCACAAATGGCTGCATGTCAACTGGG
Pea          CTCCACGGCTTCCATATCCATGCCTTGGGAGACACCACAAACGGTTGCATTTCAACTGGA
Arabidopsis  CTTCATGGTTTCCATGTCCATGCTCTTGGTGACACCACTAACGGTTGCATGTCTACTGGT
Oryza        CTCCATGGATTCCATGTGCACGCGCTCGGTGACACCACTAATGGCTGCATGTCAACTGGA
             ** ** ** *****    *  ** **    * ** ***** **  ** ** ***** ** *****

Malus        CCACACTTCAATCCTGCTGGAAAAGAGCATGGTGCCCCTGAAGATGAGCTTCGCCATGCT
Potentilla   CCACATTTCAATCCTGCTGGCAAAGAGCATGGGTCTCCTGAAGATGAGACTCGTCATGCT
Populus      CCGCATTTTAATCCTGTAGGCAAGGAAGATGGTGCCCCTGAGGATGAGAATCGTCATGCT
Pea          CCACATTTCAATCCTAATGGGAAGGAACATGGTGCCCCTGAGGATGAGACTAGACATGCT
Arabidopsis  CCACATTTCAACCCCGATGGTAAAACACACGGTGCCCCTGAGGATGCTAATCGACATGCT
Oryza        CCACACTTCAATCCTACTGGGAAGGAACATGGGGCACCACAAGATGAGAACCGCCATGCC
             ** ** ** **  **     ** **    ** **  * **  * ****     * *****

Malus        GGCGATCTTGGAAACATCACTGCTGGGGACGATGGAACTGCAACCTTCACGATTGTTGAC
Potentilla   GGTGATCTTGGAAATATCACTGTTGGGGATGACGGAACTGCTTGCTTCACAATTGTTGAC
Populus      GGTGATCTGGGAAATGTCACTGTTGGTGATGATGGCACTGCTGCTTTCACAATCATTGAC
Pea          GGTGATCTTGGAAATATCAATGTTGGTGATGATGGAACTGTAAGCTTCACCATTACTGAC
Arabidopsis  GGTGATCTAGGAAACATCACTGTTGGAGATGATGGAACTGCCACCTTCACAATCACTGAT
Oryza        GGTGATCTTGGAAATATAACAGCTGGAGCAGATGGTGTTGCTAATGTCAATGTCTCTGAC
             ** ***** *****  *  *  * ***   * ***   * **         ***  *  ***

Malus        AAGCAGATTCCTCTCGCTGGACCACACTCTATCATTGGTAGGGCGGTTGTTGTCCACGCA
Potentilla   AAACAGATTCCTCTCACTGGACCACACTCTATCATTGGTAGGGCTGTTGTTGTCCATGCA
Populus      AAACAGATTCCTCTTACTGGACCACATTCCATTATTGGTTGGGCTGTTGTTGTTCATGGA
Pea          AACCATATCCCTCTCACTGGAACAAACTCCATCATAGGAAGGGCTGTTGTTGTCCATGCC
Arabidopsis  TGCCAGATTCCTCTTACTGGACCAAACTCTATTGTTGGTTAGGGCTGTTGTTGTCCATGCA
Oryza        AGCCAGATCCCCCTTACTGGAGCACACTCCATCATTGGCCGAGCTGTTGTTGTCCATGCT
             ** ** ** **  ***** ** * ** *  *  * ** ******** **  *

Malus        CACCCTGATCACCTTGCCAACCCTGCACATCAGCTTACCAAATCCACACCAAATCCTGCT
Potentilla   GATCCTGATGACCTTGGCAAGGGTGGACATGAGCTTAGCAAATCCACTGGAAATGCTGGT
Populus      GATCCTGATGATCTTGGCAAGGGAGGACATGAACTCAGCAAAACCACTGGTAATGCTGGC
Pea          GATCCTGATGATCTTGGGAAAGGTGGTCACGAGCTTAGCAAAACTACTGGAAATGCTGGT
Arabidopsis  GACCCTGATGACCTCGGAAAGGGAGGCCATGAACTCAGCCTGGCTACTGGAAACGCAGGC
Oryza        GATCCTGATGATCTTGGCAAGGGTGGACATGAGCTTAGCAAGACCACTGGAAATGCTGGG
             ** ******** ** ** ** ** ** ** ** **  ***       *  ** ** ** **

Malus        GGCAGGGTGGCTTGCGGTATTATTGGTCTGCAAGGATGA
Potentilla   GGCAGGATAGCTTGTGGTATTATTGGCCTTCAAGGATGA
Populus      GGCAGAGTAGCATGCGGTATTATTGGTCTGCAAGGTTGA
Pea          GGCAGAGTAGCTTGTGGTATTATTGGGTTGCAAGGATAG
Arabidopsis  GGCCGTGTTGCTTGCGGCATCATTGGTCTCCAGGGCTAA
Oryza        GGCCGAGTTGCTTGCGGAATCATCGGACTCCAGGGTTAG
```

Fig. 3. Comparison of the deduced amino acid sequence of the *Potentilla* Cu/Zn SOD with sequences from other plant species. Regions of complete homology are indicated with asterisks.

```
Malus        MVKGVAVLGSSEGVKGTISFVQEGDGPTTVTGSVSGLKPGLEGFHVHALGDTTNGCMSTG
Potentilla   MAKGVAVLSSSEGVAGTILFTQEGDGPTTVTGNISGLKPGLEGFHVHALGDTTNGCMSTG
Arabidopsis  MAKGVAVLNSSEGVTGTIFFTQEGDGVTTVSGTVSGLKPGLEGFHVHALGDTTNGCMSTG
Populus      MVKAVAVLNSSEGVSGTIFFTQEGDGPTTVTGNLSGLKPGLEGFHVHALGDTTNGCMSTG
Cryza        MVKAVVVLGSSEIVKGTIHFVQEGDGPTTVTGSVSGLKPGLEGFHIHALGDTTNGCMSTG
Zea          MVKAVAVLGSSEGVKGTIFFTQEGDGPTTVTGSVSGLKPGLEGFHVHALGDTTNGCMSTG
Gossypium    MVKAVAVLGSNEGVSGTVFFSQEGDGPTTVTGNLSGLKPGLEGFHVHALGDTTNGCMSTG
Pisum        MVKAVAVLSNSNEVSGTINFSQEGNGPTTVTGTLAGLKPGLEGFHIHALGDTTNGCISTG
Soybean      MVKAVAVLGSSEGVTGTIFFTQEGNGPTTVTGSLAGLKPGLEGFHVHALGDTTNGCLSTG
             *.*.*.**...: * **: * ***:* ***:*.::**********:**********:***

Malus        PHFNPAGKEHGAPEDELRHAGDLGNITAGDDGTATFTIVDKQIPLAGPHSIIGRAVVVHA
Potentilla   PHFNPAGKEHGSPEDETRHAGDLGNITVGDDGTACFTIVDKQIPLTGPHSIIGRAVVVHA
Arabidopsis  PHFNPDGKTEGAPEDANRHAGDLGNITVGDDGTATFTITDCQIPLTGPNSIVGRAVVVHA
Populus      PHFNPVGKEFGAPEDFNRHAGDLGNVTVGDDGTAAFTIIDFQIPLTGPHSIIGRAVVVHG
Cryza        PHYNPAGKEFGAPEDETRHAGDLGNVTAGEDGVANIHVVDSQIPLTGPNSIIGRAVVVHA
Zea          PHYNPASKEFGAPEDENRHAGDLGNVTAGADGVANINVTDSQIPLTGPNSIIGRAVVVHA
Gossypium    PHFNPAGKEFGAPEDENRHAGDLGNVTVGDDGCASFSITDKQIPLTGPNSIIGRAVVVHA
Pisum        PHFNPNGKEFGAPEDETRHAGDLGNINVGDDGTVSFTITDNEIPLTGTNSIIGRAVVVHA
Soybean      AHFNPNNNEFGAPEDENRHAGDLGNVNVGDDGTVSFSITDSQIPLTGPNSIIGRAVVVHA
             .*:** .: **:***  *******:...* ** . : : * :***:*.:**:*******.

Malus        DPDDLGKGGHELSKSTGNAGGRVACGIIGLCG
Potentilla   DPDDLGKGGHELSKSTGNAGGRIACGIIGLCG
Arabidopsis  DPDDLGKGGIELSLATGNAGGRVACGIIGLCG
Populus      DPDDLGKGGHELSKTTGNAGGRVACGIIGLCG
Cryza        DPDDLGKGGHELSKTTGNAGGRVACGIIGLCG
Zea          DPDDLGKGGFELSKSTGNAGGRVACGIIGLCG
Gossypium    DPDDLGKGGHELSKSTGNAGGRVACGIIGLCG
Pisum        DPDDLCKCGHELSKTTCNACCRVACCIICLCG
Soybean      DSDDLGKGGHELSKTTGNAGGRVACGIIGLCG
             *.*********** :******:**********
```

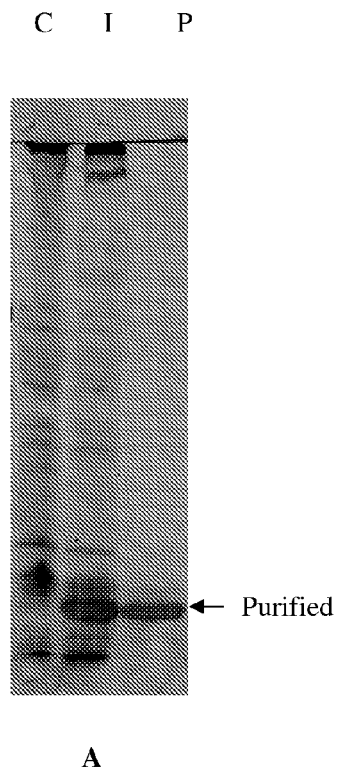
Fig.4. (A) Expression and purification of *Potentilla* SOD in *E. coli*. C, Control; I, Protein induced by IPTG; P, Purified SOD. The gel was stained by silver staining. (B) Activity staining of the gel to depict the activity of purified SOD. P, Purified SOD.

Fig-5: result of alignment of present sod gene with the sod gene of other plant species

Sequence 1: gi|311970|gi|311970I.batatas mRNA for superoxide dismutase
Length = 459 (1 .. 459)

Sequence 2: lcl|IHBT-potentilla
Length = 459 (1 .. 459)

Score =  348 bits (181),  Expect = 8e-93
 Identities = 323/394 (81%), Gaps = 0/394 (0%)
 Strand=Plus/Plus

```
Query  56   TCTTCAGCCAAGAAGGAGATGGTCCAACCACAGTCACTGGAAACGTTTCGGGCCTCAAAC  115
            ||||  ||||||| |||||||| |||| || || || |||||| ||||  |||||||| |
Sbjct  56   TCTTTACCCAAGAGGGAGATGGCCCAACTACTGTGACCGGAAACATTTCTGGCCTCAAGC  115

Query  116  CTGGTCTTCATGGCTTCCATGTCCATGCCCTAGGTGACACAACAAATGGATGCATGTCTA  175
            ||||  |||||||| ||||||| ||||| || || ||  ||||||||||  |||||| |
Sbjct  116  CTGCCCTTCATCCTTTCCATGTTCATCCTCTTGCCCACACAACCAATCCTTGCATCTCAA  175

Query  176  CTGGACCACATTTCAATCCTGCTGGAAAGGAGCATGGAGCTCCTGGAGACGATAACCGCC  235
            |||||||||||||||||||||||||| || |||||||| |||||| |||| ||| || |
Sbjct  176  CTGGACCACATTTCAATCCTGCTGGCAAAGAGCATGGGTCTCCTGAAGATGAGACTCGTC  235

Query  236  ATGCCGGTGATCTTGGAAACATCACGGTTGGAGAAGATGGTACTGCTTCATTCACCATCA  295
            |||| |||||||||||||| |||||| || ||||| |||||| ||||| ||||| || ||
Sbjct  236  ATGCTGGTGATCTTGGAAATATCACTGTTGGGGATGACGGAACTGCTTGCTTCACAATTG  295

Query  296  CTGACAAGCAGATTCCGCTTACTGGAGCAAATTCTGTTATTGGAAGAGCTGTTGTTGTTC  355
            |||||| |||||||||| ||  |||||| || | || | ||||| || |||||||||| |
Sbjct  296  TTGACAAACAGATTCCTCTCACTGGACCACACTCTATCATTGGTAGGGCTGTTGTTGTCC  355

Query  356  ATGGTGATCCCGATGATCTTGGTAAAGGTGGCCATGAGCTCAGCAAAAGCACTGGAAATG  415
            |||  ||||  ||||| |||||  ||||| |||||||||| ||||| ||||||||||||
Sbjct  356  ATGCAGATCCTGATGACCTTGGCAAGGGTGGACATGAGCTTAGCAAATCCACTGGAAATG  415

Query  416  CTGGCGGGAGGGTTGCCTGCGGTATCATTGGCCT  449
            |||| || ||| | || || |||||||||||||
Sbjct  416  CTGGTGGCAGGATAGCTTGTGGTATTATTGGCCT  449
```

> gi|38228696|emb|AJ586519.1|  Fagus sylvatica partial sod1 mRNA for superoxide dismutase
Length=710

Score =  379 bits (191),  Expect = 5e 102
 Identities = 392/459 (85%), Gaps = 0/459 (0%)
 Strand=Plus/Plus

```
Query  1    ATGGCAAAGGGCGTTGCTGTACTTAGCTCCAGTGAGGGTGTTGCTGGAACTATCCTCTTT  60
            |||||  |||| || ||||| ||||||| || ||||||||| || ||||||||| ||||
Sbjct  43   ATGGCCAAGGGTGTGGCTGTTCTTAGCTCGAATGAGGGTGTTTGTGGCACTATCTACTTT  102

Query  61   ACCCAAGAGGGAGATGGCCCAACTACTGTGACCGGAAACATTTCTGGCCTCAAGCCTGGG  120
            |||||||  |||||||||||||||| ||||| || ||||| ||||||| || || |||
Sbjct  103  GCCCAAGAAGGAGATGGCCCAACTACAGTAACTGGAAATATTTCTGGCCTTAAACCTGGA  162

Query  121  CTTCATGGTTTCCATGTTCATGCTCTTGGGGACACAACCAATGGTTGCATGTCAACTGGA  180
            || ||||| |||| ||| ||||||||||||||||||||| |||||||||||||||||||
Sbjct  163  CTCCATGGCTTCCACGTGCATGCTCTTGGGGACACAACAAATGGTTGCATGTCAACTGGA  222

Query  181  CCACATTTCAATCCTCCTGGCAAACAGCATCCGTCTCCTCAAGATCACACTCGTCATCCT  240
```

Fig 5 Continued

```
                  ||||||||||||||||||||||||||||||  ||||||||  ||||  ||  ||||||||||
Sbjct    223   CCACATTTCAATCCTGCTGGCAAAGAGCATGGTGCTCCTGAGGATGCGAATCGTCATGCT   282

Query    241   GGTGATCTTGGAAATATCACTGTTGGGGATGACGGAACTGCTTGCTTCACAATTGTTGAC   300
               ||||||||  ||||||  |||  ||||||  ||||||  ||  ||   |  ||||||||   |||||
Sbjct    283   GGTGATCTGGGAAATGTCAATGTTGGTGATGATGGCACAGTCAGTTTCACAATAATTGAC   342

Query    301   AAACAGATTCCTCTCACTGGACCACACTCTATCATTGGTAGGGCTGTTGTTGTCCATGCA   360
               ||||||||||||  ||   |||  |||  ||  ||  ||  ||  ||||||||||||||||||||||  |
Sbjct    343   AAACAGATTCCACTTTGTGGTCCAAATTCCATTATCGGAAGGGCTGTTGTTGTCCATGGA   402

Query    361   GATCCTGATGACCTTGGCAAGGGTGGACATGAGCTTAGCAAATCCACTGGAAATGCTGGT   420
               |||||  ||||||  ||||||||||||||  |||||||||  ||||||||||   ||||||||||||||||
Sbjct    403   GATCCAGATGATCTTGGCAAGGGGGACATGAACTTAGCAAGAGCACTGGAAATGCTGGT   462

Query    421   GGCAGGATAGCTTGTGGTATTATTGGCCTTCAAGGATGA   459
               |||  |  ||||||||||||||||  |||||  ||  ||||||||||
Sbjct    463   CGCCCTATACCTTCTCCTATCATTCCTCTCCAACCATCA   501
```

> gi|4102858|gb|AFC16892.1|AF016892  Populus tremuloides cytoplasmic superoxide dismutase
1 (SODcyt1)
mRNA, complete cds
Length=787

Score =  333 bits (168),  Expect = 3e-88
 Identities = 342/400 (85%), Gaps = 0/400 (0%)
 Strand=Plus/Plus

```
Query    56    TCTTTACCCAAGAGGGAGATGGCCCAACTACTGTGACCGGAAACATTTCTGGCCTCAAGC   115
               ||||||||||||  ||||||||||||||||||||||  |   ||||||  |||||||  ||  ||||
Sbjct    134   TCTTTACCCAACAAGCACATCGCCCAACTACTCTAATTCCAAACCTTTCTCGTCTTAACC   193

Query    116   CTGGGCTTCATGGTTTCCATGTTCATGCTCTTGGGGACACAACCAATGGTTGCATGTCAA   175
               |  ||  ||||||||||  |||||  ||  ||||||  |||||  |||||  ||  ||||||  ||||||||||
Sbjct    194   CAGGCCTTCATGGCTTCCACGTCCATGCCCTTGGAGACACCACAAATGGCTGCATGTCAA   253

Query    176   CTGGACCACATTTCAATCCTGCTGGCAAAGAGCATGGGTCTCCTGAAGATGAGACTCGTC   235
               ||||  ||  |||||  ||||||||  |||||  ||||||||  |  |||||  ||||||||  |||||
Sbjct    254   CTGGGCCGCATTTTAATCCTGTAGGCAAGGAGCATGGTGCCCCTGAGGATGAGAATCGTC   313

Query    236   ATGCTGGTGATCTTGGAAATATCACTGTTGGGGATGACGGAACTGCTTGCTTCACAATTG   295
               ||||||||||||  ||||||  ||||||||||||  |||||  ||  ||||||   ||||||||
Sbjct    314   ATGCTGGTGATCTGGGAAATGTCACTGTTGGTGATGATGGCACTGCTGCTTTCACAATCA   373

Query    296   TTGACAAACAGATTCCTCTCACTGGACCACACTCTATCATTGGTAGGGCTGTTGTTGTCC   355
               ||||||||||||||||||||  |||||||||  ||  ||  ||||||||||||||||||||  |
Sbjct    374   TTGACAAACAGATTCCTCTTACTGGACCACATTCCATTATTGGTTGGGCTGTTGTTGTTC   433

Query    356   ATGCAGATCCTGATGACCTTGGCAAGGGTGGACATGAGCTTAGCAAATCCACTGGAAATG   415
               |||  ||||||||||||||||  |||||||||||||||  ||||||||  ||||||  |  |||| 
Sbjct    434   ATGGAGATCCTGATGATCTTGGCAAGGGAGGACATGAACTCAGCAAAACCACTGGTAATG   493

Query    416   CTGGTGGCAGGATAGCTTGTGGTATTATTGGCCTTCAAGG   455
               ||||  |||||  ||||  ||  ||||||||||  ||  |||||
Sbjct    494   CTGGCGGCAGAGTAGCATGCGGTATTATTGGTCTGCAAGG   533
```

> gi|50540928|gb|AY642137.1|  Manihot esculenta copper/zinc superoxide dismutase mRNA,
complete
cds
Length=774

Score =  333 bits (168),  Expect = 3e-88
 Identities = 354/416 (85%), Gaps = 0/416 (0%)
 Strand=Plus/Plus

```
Query    31    AGTGAGGGTGTTGCTGGAACTATCCTCTTTACCCAAGAGGGAGATGGCCCAACTACTGTG   90
               ||||||||||||||||||  ||  |||  ||||  |||||||||  ||||||||||  ||||||  ||  ||
```

Fig 5 Continued

```
Sbjct   44   AGTGAGGGTGTTGCTGGGACAATCTTCTTCACCCAAGAAGGAGATGGTCCAACCACCGTC   103

Query   91   ACCGGAAACATTTCTGGCCTCAAGCCTGGGCTTCATGGTTTCCATGTTCATGCTCTTGGG   150
             ||  ||||   ||||||||||||| |||||  |||||||||| |||||||||||| |||||
Sbjct  104   ACTCCAACTCTTTCTCGCCCTTAAGCCACGCGCTTCATCGATTCCATCTTCATGCCCTTCCA   163

Query  151   GACACAACCAATGGTTGCATGTCAACTGGACCACATTTCAATCCTGCTGGCAAAGAGCAT   210
             ||||||||| |||||||||||||||||||  ||||||||||  ||||||||||||||||||
Sbjct  164   GACACAACAAATGGTTGCATGTCAACTGGGCCACATTTCAACCCTGGTGGCAAAGAGCAT   223

Query  211   GGGTCTCCTGAAGATGAGACTCGTCATGCTGGTGATCTTGGAAATATCACTGTTGGGGAT   270
             ||   ||||||  ||  |   ||||||||||||||||||||||| |||||| |||||| ||   |||
Sbjct  224   GGTGCCCCTGAGGACGACATTCGTCATGCTGGTGATCTGGGAAATGTCACTGCTGGTGAT   283

Query  271   GACGGAACTGCTTGCTTCACAATTGTTGACAAACAGATTCCTCTCACTGGACCACACTCT   330
             ||  || |||||| | |||||||||  |||||||||| |||||||||  ||||| || || ||
Sbjct  284   GATGGCACTGCTAGTTTCACAATCGTTGACAAGGATATTCCTCTTTCTGGTCCGCATTCC   343

Query  331   ATCATTGGTAGGCTGTTGTTGTCCATGCAGATCCTGATGACCTTGGCAAGGGTGGACAT   390
             ||   | || |||||| || ||||| ||||||||||||||||||  ||||| ||||| ||||||
Sbjct  344   ATTGTAGGAAGGGCAGTCGTTGTTCATGCAGATCCTGATGATCTTGGAAAGGGGGGACAT   403

Query  391   GAGCTTAGCAAATCCACTGGAAATGCTGGTGGCAGGATAGCTTGTGGTATTATTGG     446
             || |||||||||  |||||||||||||||||||||||   |||| |||||| ||||||||
Sbjct  404   GAACTTAGCAAAACCACTGGAAATGCTGGTGGCAGGGTAGCATGTGGTGTTATTGG     459
```

> gi|6723475|emb|AJ279694.1|BPE279694   Betula pendula partial mRNA for copper/zinc-
superoxide dismutase
(cu/Zn sod gene)
Length=355

Score =  323 bits (163),  Expect = 3e-85
Identities = 289/331 (87%),  Gaps = 0/331 (0%)
Strand=Plus/Plus

```
Query   49   ACTATCCTCTTTACCCAAGAGGGAGATGGCCCAACTACTGTGACCGGAAACATTTCTGGC   108
             |||||||  ||||||||||||   ||||||||||||||  ||||  ||||| ||||||||||
Sbjct   25   ACTATCCACTTTACCCAAGAAGCTGATGGCCCAACTACAGTAACTGGAAATATTTCTGGC   84

Query  109   CTCAAGCCTGGGCTTCATGGTTTCCATGTTCATGCTCTTGGGGACACAACCAATGGTTGC   168
             || |||||||  ||||| ||||||| ||||| ||||| |||| ||||||||||||||||||
Sbjct   85   CTTAACCCTGCCCTCCATGCGTTCCATCTCCATCCACTTCGGGACACAACAAATGGTTCC   144

Query  169   ATGTCAACTGGACCACATTTCAATCCTGCTGGCAAAGAGCATGGGTCTCCTGAAGATGAG   228
             |||||||||||| ||||||||||||||||||||||||||||||||  ||||||| ||||||
Sbjct  145   ATGTCAACTGGGCCACATTTCAATCCTGCTGGCAAAGAGCATGGTGCTCCTGAGGATGAG   204

Query  229   ACTCGTCATGCTGGTGATCTTGGAAATATCACTGTTGGGGATGACGGAACTGCTTGCTTC   288
             |  ||||||||  |||||||||||||||| ||||| |||| ||  ||||| |||||| |||
Sbjct  205   AATCGTCATGCCGGTGATCTGGGAAATGTCACCGTTGGTGATGATGGTACTGCCAGTTTC   264

Query  289   ACAATTGTTGACAAACAGATTCCTCTCACTGGACCACACTCTATCATTGGTAGGGCTGTT   348
             ||||| ||||||||  |||||||  ||||||||||||| |||| ||||| ||||||||||
Sbjct  265   ACAATAGTTGACAAGCAGATTCCACTTTCTGGACCACATTCTATTATTGGAAGGGCTGTT   324

Query  349   GTTGTCCATGCAGATCCTGATGACCTTGGCA   379
             ||||||| |  ||||| ||||| |||||||
Sbjct  325   GTTGTCCACGGGGATCCAGATGATCTTGGCA   355
```

> gi|13274149|emb|AJ278669.1|PTR278669   Populus tremula x Populus tremuloides mRNA for
putative cytosolic
CuZn superoxide dismutase (cyt SOD1 gene)
Length=851

Score =  305 bits (154),  Expect = 6e-80
Identities = 331/390 (84%),  Gaps = 0/390 (0%)
Strand=Plus/Plus

Fig 5 Continued

```
Query   57   CTTTACCCAAGAGGGAGATGGCCCAACTACTGTGACCGGAAACATTTCTGGCCTCAAGCC   116
             |||||||||||| ||||||||| ||||||||||| || |||| | | ||| || |||||
Sbjct  135   CTTTACCCAAGAAGGAGATGGTCCAACTACTGTAACTGGAAGCCTCTGTGGTCTTAAGCC   194

Query  117   TGGGCTTCATGGTTTCCATGTTCATGCTCTTGGGCACACAACCAATGGTTGCATGTCAAC   176
             || ||||||||| |||||||||||||| ||||| ||||| ||||| |||||||||||||
Sbjct  195   AGGCCTTCATGGCTTCCATGTTCATGCCCTTGGAGACACCACAAATGGCTGCATGTCAAC   254

Query  177   TGGACCACATTTCAATCCTGCTGGCAAAGAGCATGGGTCTCCTGAAGATGAGACTCGTCA   236
             ||| || ||||| |||||||   |||||||||||||   | |||||| |||||| |||||
Sbjct  255   TGGCCCGCATTTTAATCCTGTAGGCAAAGAGCATGGTGCCCCTGAGGATGAGAATCGTCA   314

Query  237   TGCTGGTGATCTTGGAAATATCACTGTTGGGGATGACGGAACTGCTTGCTTCACAATTGT   296
             |||||||||| | ||||||| |||||||| |||||||  || ||    || |||| |
Sbjct  315   TGCTGGTGATTTGGGAAATGTCACTGTTGGTGATGATGGCACCGCTACTGTCTCAATCAT   374

Query  297   TGACAAACAGATTCCTCTCACTGGACCACACTCTATCATTGGTAGGGCTGTTGTTGTCCA   356
             ||||||  |||||||||||||||||||||| | || |||| |||||||||||||||| ||
Sbjct  375   TGACAACCAGATTCCTCTCACTGGACCAAATTCCATCGTTGGAAGGGCTGTTGTTGTTCA   434

Query  357   TGCAGATCCTGATGACCTTGGCAAGGGTGGACATGAGCTTAGCAAATCCACTGGAAATGC   416
             ||||||||||||||| ||||||||||| ||||||||| |||||||| || |||| |||||
Sbjct  435   TGCAGATCCTGATGATCTTGGCAAGGGAGGACATGAACTTAGCAAAAGCACTGGTAATGC   494

Query  417   TCCTCCCACCATACCTTGTCGTATTATTCG   446
             |||||||||| |||| |||||| |||||||
Sbjct  495   TGGTGGCAGAGTAGCATGTGGTGTTATTGG   524
```

>☐ gi|53748478|emb|AJ844003.1|  Plantago major mRNA for copper-zinc superoxide dismutase
(csd1
gene)
Length=779

Score =  305 bits (154),  Expect = 6e-80
Identities = 373/446 (83%), Gaps = 0/446 (0%)
Strand=Plus/Plus

```
Query    7   AAGGGCGTTGCTGTACTTAGCTCCAGTGAGGGTGTTGCTGGAACTATCCTCTTTACCCAA   66
             ||||| ||||| || ||||||  ||||||||||||| ||  ||| ||||| ||||||||
Sbjct   70   AAGGGTGTTGCAGTGCTTAGCAGCAGTGAGGGTGTTAGTGGCACCGTCCTCTTTTCCCAA   129

Query   67   GAGGGAGATGGCCCAACTACTGTGACCGGAAACATTTCTGGCCTCAAGCCTGGGCTTCAT   126
             || ||||| || || || |||| || ||||||  ||||||||||||||| |||| |||||
Sbjct  130   GAAGGAGAAGGACCCACCACTGTAACTGGAAACCTTTCTGGCCTTAAGCCTGGACTTCAC   189

Query  127   GGTTTCCATGTTCATGCTCTTGGGGACACAACCAATGGTTGCATGTCAACTGGACCACAT   186
             || |||||||||||||||||||| |||||  |||||| ||||||||||| ||||||||||
Sbjct  190   GGCTTCCATGTTCATGCTCTTGGTGACACTACCAACGGTTGCATGTCAACAGGACCACAT   249

Query  187   TTCAATCCTGCTGGCAAAGAGCATGGGTCTCCTGAAGATGAGACTCGTCATGCTGGTGAT   246
             ||||||||  |||  |||||||||||| ||  |||||| |||||  ||| ||||||||||
Sbjct  250   TTCAATCCGGCTGCAAAAGAGCATGGTGCTCCTGATGATGAGGTTCGCCATGCTGGTGAC   309

Query  247   CTTGGAAATATCACTGTTGGGGATGACGGAACTGCTTGCTTCACAATTGTTGACAAACAG   306
             ||||| |||  || |||| || ||||| ||||||| |||||||| ||||||||| | ||
Sbjct  310   CTTGGTAATGTCACAGTGGGAGATGATGGAACTGCAAGTTTCACCATTGTTGACAAGCTG   369

Query  307   ATTCCTCTCACTGGACCACACTCTATCATTGGTAGGGCTGTTGTTGTCCATGCAGATCCT   366
             ||||| ||  |||||||||||| |||| ||||| ||||||||||||||||| || ||
Sbjct  370   ATTCCGCTGACTGGACCACATTCCATCATTGGAAGGGCTGTTGTTGTCCATGCTGACCCC   429

Query  367   GATGACCTTGGCAAGGGTGGACATGAGCTTAGCAAATCCACTGGAAATGCTGGTGGCAGG   426
             |||||   || | |||||||||||||| || |||||| | |||||||||||||||| ||
Sbjct  430   GATGATTTGGGAAGGGGTGGACATGAACTCAGCAAAACTACCGGAAATGCTGGTGGAAGA   489

Query  427   ATAGCTTGTGGTATTATTGGCCTTCA   452
             | |||||||||||| ||||| |||||
Sbjct  490   GTTGCTTGTGGTATCATTGGTCTTCA   515
```

Fig 5 Continued

```
>    gi|5726591|gb|AF170297.1|AF170297  Manihot esculenta copper/zinc-superoxide dismutase
mRNA, complete
cds
Length=801

Score =  295 bits (149),  Expect = 6e-77
 Identities = 338/401 (84%),  Gaps = 0/401 (0%)
 Strand=Plus/Plus Query  46   GGAACTATCCTCTTTACCCAAGAGGGAGATGGCCCAACTACTGTGACCGGAAACATTTCT  105
            ||||| ||| |||||||||||||| |||||||| || || ||||| || |||||||||||
Sbjct  100  GGAACAATCTTCTTTACCCAAGAAGGAGATGGTCCTACCACTGTAACTGGAAACATTTCC  159

Query  106  CCCCTCAAGCCTGCGCTTCATCGTTTCCATCTTCATGCTCTTGGGCACACAACCAATCCT  165
            ||||| ||||| ||||||||||||||||| ||||| ||||| ||||| |||||||| |||
Sbjct  160  GGCCTTAAGCCAGGGCTTCATGGGTTCCACGTCCATGCCCTTGGAGACACAACAAACGGT  219

Query  166  TGCATGTCAACTGGACCACATTTCAATCCTGCTGGCAAAGAGCATGGGTCTCCTGAAGAT  225
            |||||||||||||| ||||| || || ||| |||||||||| ||||| | |||||| |||
Sbjct  220  TGCATGTCAACTGGGCCACACTTTAACCCTTCTGGCAAAGATCATGGTGCCCCTGAGGAT  279

Query  226  GAGACTCGTCATGCTGGTGATCTTGGAAATATCACTGTTGGGGATGACGGAACTGCTTGC  285
            |||| |||||||||||||||||||| |||||| |||||| ||||| || ||||||| |
Sbjct  280  GAGATTCGTCATGCTGGTGATCTGGGAAATGTCACTGCTGGTGATGATGGCACTGCTAGT  339

Query  286  TTCACAATTGTTGACAAACAGATTCCTCTCACTGGACCACACTCTATCATTGGTAGGGCT  345
            ||||||||| |||||||| || ||||||||  |||| | | || ||||| || |||||
Sbjct  340  TTCACAATTATTGACAAGCATATTCCTCTTTCTGGTCAAAATTCAATCATAGGAAGGGCA  399

Query  346  GTTGTTGTCCATGCAGATCCTGATGACCTTGGCAAGGGTGGACATGAGCTTAGCAAATCC  405
            |||||||| |||||||||||||||||| |||||| ||| |||||||||||| || ||| |
Sbjct  400  GTTGTTGTTCATGCAGATCCTGATGATCTTGGCAGGGGAGGACATGAACTCAGTAAAACC  459

Query  406  ACTGGAAATGCTGGTGGCAGGATAGCTTGTGGTATTATTGG  446
            || |||||||||||||||||||| |||| || |||||||||
Sbjct  460  ACCGGAAATGCTGGTGGCAGAGTAGCATGCGGTATTATTGG  500

>    gi|56549630|gb|AY833718.1|  Codonopsis lanceolata CuZn superoxide dismutase (SODCc)
mRNA,
complete cds
Length=799

Score =  289 bits (146),  Expect = 4e-75
 Identities = 335/398 (84%),  Gaps = 0/398 (0%)
 Strand=Plus/Plus Query  58   TTTACCCAAGAGGGAGATGGCCCAACTACTGTGACCGGAAACATTTCTGGCCTCAAGCCT  117
            |||||||||||||||||||||||||||| || || |||| | |||||||||||| | |||
Sbjct  212  TTTACCCAAGAGGGAGATGGCCCAACTAAAGTTACTGGAAGCCTTTCTGGCCTTCAACCT  271

Query  118  CGCCTTCATCGTTTCCATCTTCATGCTCTTGGGCACACAACCAATCCTTCCATCTCAACT  177
            | | ||| |||||||||||||| ||||| |||||||||||||||||||||||||||||||
Sbjct  272  GGACCTCACGGTTTCCATGTTCATGCCCTTGGTGACACAACCAATGGTTGCATGTCAACT  331

Query  178  GGACCACATTTCAATCCTGCTGGCAAAGAGCATGGGTCTCCTGAAGATGAGACTCGTCAT  237
            || || |||| ||||||||||||| |||| ||||| |||||||| ||||| |||||||||
Sbjct  332  GGTCCTCATTATAATCCTGCTGGAAAAGAACATGGTGCTCCAGAGGACGAGATTCGTCAT  391

Query  238  GCTGGTGATCTTGGAAATATCACTGTTGGGGATGACGGAACTGCTTGCTTCACAATTGTT  297
            |||||||| || || ||| | || || || ||||| |||| ||||||||  ||||| |||
Sbjct  392  GCTGGTGACCTCGGGAATGTTACAGTAGGCGAAGACGGTACTGCAAATTTCACCATCGTT  451

Query  298  GACAAACAGATTCCTCTCACTGGACCACACTCTATCATTGGTAGGGCTGTTGTTGTCCAT  357
            ||||| ||||| ||||||||  |||| | ||||||||||||||| ||||||||||||||
Sbjct  452  GACAACCAGATTCCACTATCTGGACCTCATTCTATCATTGGAAGGGCTGTAGTTGTCCAT  511

Query  358  GCAGATCCTGATGACCTTGGCAAGGGTGGACATGAGCTTAGCAAATCCACTGGAAATGCT  417
```

Fig 5 Continued

```
                  || ||||||||||| ||||| |||||||| ||||| || |||||| ||||||||||||
Sbjct    512  GCTGATCCTGATGATCTTGGAAAGGGTGGCCATGAACTCAGCAAAAGCACTGGAAATGCT   571

Query    418  GGTGGCAGGATAGCTTGTGGTATTATTGGCCTTCAAGG   455
              |||||||||||| || |||||||| ||||| || |||||
Sbjct    572  GGTGGCAGGATTGCCTGTGGTATCATTGGACTGCAAGG   609

>☐ gi|74229676|gb|DQ088818.1|  Gossypium hirsutum cytoplasmic Cu/ZnSOD mRNA, complete cds
Length=459

Score =  289 bits (146),  Expect = 4e-75
 Identities = 331/394 (84%), Gaps = 0/394 (0%)
 Strand=Plus/Plus Query     62  CCCAAGAGGGAGATGGCCCAACTACTGTGACCGGAAACATTTCTGGCCTCAAGCCTGGGC   121
              ||||||| |||||||| ||||||||| ||||| || ||| ||||||| || ||||| || |
Sbjct     62  CCCAAGAAGGAGATGGTCCAACTACCGTGACTGGGAACCTTTCTGGTCTTAAGCCGGGAC   121

Query    122  TTCATGGTTTCCATGTTCATGCTCTTGGGGACACAACCAATGGTTGCATGTCAACTGGAC   181
              | |||||  |||||||||||||  ||||||||||||||| || || |||||||||||||||
Sbjct    122  TCCATGGCTTCCATGTTCATGCCCTTGGGGACACAACTAACGGGTGCATGTCAACTGGAC   181

Query    182  CACATTTCAATCCTGCTGGCAAAGAGCATGGGTCTCCTGAAGATGAGACTCGTCATGCTG   241
              | |||||  ||||||||||||||||||||||| |||| |||||||||||  || |||||||
Sbjct    182  CCCATTTTAATCCTGCTGGCAAAGAGCATGGTGCTCCNGAAGATGAGAACCGCCATGCTG   241

Query    242  GTGATCTTGGAAATATCACTGTTGGGGATGACGGAACTGCTTGCTTCACAATTGTTGACA   301
              |||||||  || |||  |||||||||| ||||| |||    ||| |||||| | ||    ||||
Sbjct    242  GTGATCTAGGNAATGTCACTGTTGGTGATGATGGCTGTGCNAGCTTCTCCATCACCGACA   301

Query    302  AACAGATTCCTCTCACTGGACCACACTCTATCATTGGTAGGGCTGTTGTTGTCCATGCAG   361
              |||||||||| | |||| ||||  || || || || || || ||||| |||||||||||||
Sbjct    302  AACAGATTCCNCTCACAGGCCCAAACTCCATTATCGGAAGAGCTGTAGTTGTCCATGCAG   361

Query    362  ATCCTGATGACCTTGGCAAGGGTGGACATGAGCTTAGCAAATCCACTGGAAATGCTGGTG   421
              |||| |||||||||||||||||| | ||||||||||| |||||   ||| |||||||||| |
Sbjct    362  ATCCCGATGACCTTGGCAAGGGCGGCCATGAGCTCAGCAAAAGCACAGGAAATGCTGGCG   421

Query    422  GCAGGATAGCTTGTGGTATTATTGGCCTTCAAGG   455
              |||| ||||||| ||||||||||||| || |||||
Sbjct    422  GCAGAGTAGCTTGCGGTATTATTGGTCTGCAAGG   455

>☐ gi|73665954|gb|DQ124227.1|  Fagus sylvatica putative copper/zinc-superoxide dismutase mRNA,
partial cds
Length=388

Score =  283 bits (143),  Expect = 2e-73
 Identities = 284/331 (85%), Gaps = 0/331 (0%)
 Strand=Plus/Plus Query     57  CTTTACCCAAGAGGGAGATGGCCCAACTACTGTGACCGGAAACATTTCTGGCCTCAAGCC   116
              |||| |||||||| ||||||||||||||||||| || || ||||| |||||||||| || ||
Sbjct     58  CTTTGCCCAAGAAGGAGATGGCCCAACTACAGTAACTGGAAATATTTCTGGCCTTAAACC   117

Query    117  TGGGCTTCATGGTTTCCATGTTCATGCTCTTGGGGACACAACCAATGGTTGCATGTCAAC   176
              ||| || ||||| ||||| || |||| ||||||||||||||||  ||||||||||||||||
Sbjct    118  TGGACTCCATGGCTTCCACGTGCATGCTCTTGGGGACACAACAAATGGTTGCATGTCAAC   177

Query    177  TGGACCACATTTCAATCCTGCTGGCAAAGAGCATGGGTCTCCTGAAGATGAGACTCGTCA   236
              |||||||||||||||||||||||||||||| |||||   |||||| |||| |||  || ||
Sbjct    178  TGGACCACATTTCAATCCTGCTGGCAAAGGGCATGGTGCTCCTGAGGATGCGAATCGTCA   237

Query    237  TGCTGGTGATCTTGGAAATATCACTGTTGGGGATGACGGAACTGCTTGCTTCACAATTGT   296
              ||||||||||||| ||||| || |||||| | |||||| || |     | |||||||| |
Sbjct    238  TGCTGGTGATCTGGGAAATGTCAATGTTGGTGATGATGGCACAGTCAGTTTCACAATAAT   297
```

Fig 5 Continued

```
Query  297  TGACAAACAGATTCCTCTCACTGGACCACACTCTATCATTGGTAGGGCTGTTGTTGTCCA  356
            ||||||||||||| ||   ||| ||| | || || || ||  ||||||||||||||||||
Sbjct  298  TGACAAACAGATTCCACTTTGTGGTCCAAATTCCATTATCGGAAGGGCTGTTGTTGTCCA  357

Query  357  TGCAGATCCTGATGACCTTGGCAAGGGTGGA  387
            || |||||| |||||  ||||||||||||||
Sbjct  358  TGGAGATCCAGATGATCTTGGCAAGGGTGGA  388

>  gi|33340235|gb|AF318938.1|  Citrus limon copper/zinc superoxide dismutase mRNA, complete
cds
Length=744

Score =  283 bits (143),  Expect = 2e-73
 Identities = 335/399 (83%), Gaps = 0/399 (0%)
 Strand=Plus/Plus Query  57   CTTTACCCAAGAGGGAGATGGCCCAACTACTGTGACCGGAAACATTTCTGGCCTCAAGCC  116
            ||||||||| || |||||||||| ||||| |||||  | |||| | | |||||||||||
Sbjct  184  CTTTACCCAGGAAGGAGATGGTCCAACAACTGTTTCAGGAAGCCTCTCTGGTCTCAAGCC  243

Query  117  TGGGCTTCATGGTTTCCATGTTCATGCTCTTGGGGACACAACCAATGGTTGCATGTCAAC  176
            ||| | |||||| | ||||||||||||||||||| |||||||||  |||||||||||  
Sbjct  244  TGGTCCTCATGGATTCCATGTTCATGCTCTTGGAGACACAACAAATGGTTGCATGTCTAC  303

Query  177  TGGACCACATTTCAATCCTGCTGGCAAAGAGCATGGGTCTCCTGAAGATGAGACTCGTCA  236
            ||||| || ||  ||  ||||||||| ||||| ||||   |||| |||   |||| |||
Sbjct  304  TGGACCCCACTTTAACCCTGCTGGAAAAGAACATGGAGCTCCAGAGGATGATAATCGTCA  363

Query  237  TGCTGGTGATCTTGGAAATATCACTGTTGGGGATGACGGAACTGCTTGCTTCACAATTGT  296
            |||||||||| | |||||| |||  |||| | |||||| |||||| || |||   ||||
Sbjct  364  TGCTGGTGATTTAGGAAATGTCAATGTTAGTGATGATGGTACTGCTACTTTTACAGTTGT  423

Query  297  TGACAAACAGATTCCTCTCACTGGACCACACTCTATCATTGGTAGGGCTGTTGTTGTCCA  356
            |||||| ||||||||||| |||||||| ||||| |||||||||| ||||||||| ||||
Sbjct  424  TGACAATCAGATTCCTCTTTCTGGACCAAATTCCATTATTGGAAGGGCTGTTGTAGTCCA  483

Query  357  TGCAGATCCTGATGACCTTGGCAAGGGTGGACATGAGCTTAGCAAATCCACTGGAAATGC  416
            |||||||| ||||||||||||||||| ||| ||||| |||| ||| |||||||||||||
Sbjct  484  CGCAGATCCCGATGATCTTGGCAAGGGCGGTCATGAGCTGAGCAAAACCACTGGAAATGC  543

Query  417  TCCTCCCACCATAGCTTCTGGTATTATTGCCCTTCAACC  455
            |||||||| ||||| || ||||| || ||||||| ||||
Sbjct  544  TGGTGGCAGAGTAGCTTGCGGCATAATTGGCCTCCAAGG  582

>  gi|17385627|dbj|AB062752.1|  Bruguiera gymnorhiza SodC mRNA for copper/zinc superoxide
dismutase,
complete cds
Length=874

Score =  283 bits (143),  Expect = 2e-73
 Identities = 317/375 (84%), Gaps = 0/375 (0%)
 Strand=Plus/Plus Query  63   CCAAGAGGGAGATGGCCCAACTACTGTGACCGGAAACATTTCTGGCCTCAAGCCTGGGCT  122
            |||||||||||||||||||||||||||| ||||| |||||||||||||  ||| | ||||
Sbjct  202  CCAAGAGGGAGATGGCCCAACTACTGTAACTGGAAATGTTTCTGGCCTTAAGTCAGGGCT  261

Query  123  TCATGGTTTCCATGTTCATGCTCTTGGGGACACAACCAATGGTTGCATGTCAACTGGACC  182
            ||||| | |||||||||||||||||||||||||| ||||||||||||||||||| || ||
Sbjct  262  TCATGGCTTCCATGTTCATGCTCTTGGGGACACTACAAATGGTTGCATGTCAACTGGGCC  321

Query  183  ACATTTCAATCCTGCTGGCAAAGAGCATGGGTCTCCTGAAGATGAGACTCGTCATGCTGG  242
             | |||||||||| |||| ||||||||||| |  ||||| || || ||| ||||||| ||
Sbjct  322  GCACTTCAATCCAGGTAGCAAAGAGCATGGTGCCCCTGAAGACGAGAACCGTCATGCCGG  381

Query  243  TGATCTTGGAAATATCACTGTTGGGGATGACGGAACTGCTTGCTTCACAATTGTTGACAA  302
            ||| || |||||| | | ||||| |||||| || ||||| ||||||   |||||||||||
```

Fig 5 Continued

```
Sbjct  382  TGACCTAGGAAATGTAAATGTTGCGGATGATGGCACTGCAACATTCACAATCACTGACAA  441

Query  303  ACACATTCCTCTCACTGCACCACACTCTATCATTGCTACCCCTCTTGTTCTCCATCCACA  362
            |||||||||| ||||||||| | || ||  |||| ||||||||||||| ||||| ||
Sbjct  442  TCAGATTCCTCTTACTGGACCCAATTCCATTGTTGGAAGGGCTGTTGTTGTTCATGCTGA  501

Query  363  TCCTGATGACCTTGGCAAGGGTGGACATGAGCTTAGCAAATCCACTGGAAATGCTGGTGG  422
            |||||||||  || ||||||| ||  ||||| ||||||||||   ||||||||||||||
Sbjct  502  TCCTGATGATCTGGGCAAGGGAGGGCATGAACTTAGCAAAAGCACTGGAAATGCTGGTGG  561

Query  423  CAGGATAGCTTGTGG  437
            |||| |||| |||||
Sbjct  562  CAGGGTAGCATGTGG  576
```

>☐ gi|52313439|dbj|AB190501.1| Populus alba x Populus tremula var. glandulosa CuZn SOD
mRNA
for CuZn-superoxide dismutase, complete cds, clone: PO3024C12
Length=730

Score =  281 bits (142),  Expect = 9e-73
 Identities = 328/390 (84%), Gaps = 0/390 (0%)
 Strand=Plus/Plus

```
Query  57   CTTTACCCAAGAGGGAGATGGCCCAACTACTGTGACCGGAAACATTTCTGGCCTCAAGCC  116
            |||||||||||| |||||||||| |||||||||| || |||| | | | ||| || |||||
Sbjct  134  CTTTACCCAAGAAGGAGATGGTCCAACTACTGTAACTGGAAGCCTCTGTGGTCTTAAGCC  193

Query  117  TGGGCTTCATGGTTTCCATGTTCATGCTCTTGGGGACACAACCAATGGTTGCATGTCAAC  176
             | ||||||||| ||||||||||||||| || |||| ||||| || ||||| ||||||||
Sbjct  194  AGGCCTTCATGGCTTCCATGTTCATGCCCTTGGAGACACCACAAATGGCTGCATGTCAAC  253

Query  177  TGGACCACATTTCAATCCTGCTGGCAAAGAGCATGGGTCTCCTGAAGATGAGACTCGTCA  236
            ||| || ||||| |||||||| |||||||||||||| | ||||| ||||||| ||||||
Sbjct  254  TGGCCCGCATTTTAATCCTGTAGGCAAAGAGCATGGTGCCCCTGAGGATGAGAATCGTCA  313

Query  237  TGCTGGTGATCTTGGAAATATCACTGTTGGGGATGACGGAACTGCTTGCTTCACAATTGT  296
            ||||||||||| | |||||| ||||||| | |||||| ||||  ||||      || || |
Sbjct  314  TGCTGGTGATTTGGGAAATGTCACTGTTGGTGATGATGGCACCGCTACTGTCTCAATCAT  373

Query  297  TGACAAACAGATTCCTCTCACTGGACCACACTCTATCATTGGTAGGGCTGTTGTTGTCCA  356
            |||||| |||||||||| |||||||||| ||||||||||| ||  |||| ||||| ||
Sbjct  374  TGACAACCAGATTCCTCTTACTGGACCAAATTCCATTGTTGGAAGGGCAGTTGTTGTTCA  433

Query  357  TGCAGATCCTGATGACCTTGGCAAGGGTGGACATGAGCTTAGCAAATCCACTGGAAATGC  416
            ||||||||||||||| |||||||||||||||||| ||| |||||||| ||||| |||||
Sbjct  434  TGCAGATCCTGATGATCTTGGCAAGGGAGGACATGAACTTAGCAAAAGCACTGGTAATGC  493

Query  417  TGGTGGCAGGATAGCTTGTGGTATTATTGG  446
            ||||||||| |||| |||||| ||||||||
Sbjct  494  TGGTGGCAGAGTAGCATGTGGTGTTATTGG  523
```

>☐ gi|52313437|dbj|AB190500.1| Populus alba x Populus tremula var. glandulosa CuZn-SOD
mRNA
for CuZn-superoxide dismutase, complete cds, clone: PO3023E02
Length=725

Score =  281 bits (142),  Expect = 9e-73
 Identities = 328/390 (84%), Gaps = 0/390 (0%)
 Strand=Plus/Plus

```
Query  57   CTTTACCCAAGAGGGAGATGGCCCAACTACTGTGACCGGAAACATTTCTGGCCTCAAGCC  116
            |||||||||||| |||||||||| |||||||||| || |||| | | | ||| || |||||
Sbjct  154  CTTTACCCAAGAAGGAGATGGTCCAACTACTGTAACTGGAAGCCTCTGTGGTCTTAAGCC  213

Query  117  TGGGCTTCATGGTTTCCATGTTCATGCTCTTGGGGACACAACCAATGGTTGCATGTCAAC  176
             | ||||||||| ||||||||||||||| || |||| ||||| || ||||| ||||||||
Sbjct  214  AGGCCTTCATGGCTTCCATGTTCATGCCCTTGGAGACACCACAAATGGCTGCATGTCAAC  273
```

Fig 5 Continued

```
Query    177  TGGACCACATTTCAATCCTGCTGGCAAAGAGCATGGGTCTCCTGAAGATGAGACTCGTCA  236
              ||| || |||||| |||||||  ||||||||||||||| | |||||| ||||||| ||||||
Sbjct    274  TGGCCCGCATTTTAATCCTGTAGGCAAAGAGCATGGTGCCCCTGAGGATGAGAATCGTCA  333

Query    237  TGCTGGTGATCTTGGAAATATCACTGTTGGGGATGACGGAACTGCTTGCTTCACAATTGT  296
              ||||||||||| | |||||| |||||||||||| ||||| || || |||    || |||| |
Sbjct    334  TGCTGGTGATTTGGGAAATGTCACTGTTGGTGATGATGGCACCGCTACTGTCTCAATCAT  393

Query    297  TGACAAACAGATTCCTCTCACTGGACCACACTCTATCATTGGTAGGGCTGTTGTTGTCCA  356
              ||||||  |||||||| ||||||||  | || || |||| ||||| |||||| ||||||| ||
Sbjct    394  TGACAACCAGATTCCTCTTACTGGACCAAATTCCATTGTTGGAAGGGCAGTTGTTGTTCA  453

Query    357  TCCAGATCCTGATGACCTTCGCCAAGCGTGCACATGACCTTACCAAATCCACTGGAAATCC  416
              |||||||||||||||| ||||||||||| ||||||||  ||||||||| |||||| |||||
Sbjct    454  TGCAGATCCTGATGATCTTGGCAAGGGAGGACATGAACTTAGCAAAAGCACTGGTAATGC  513

Query    417  TGGTGGCAGGATAGCTTGTGGTATTATTGG    446
              ||||||||| |||| ||||  |||||||||
Sbjct    514  TGGTGGCAGAGTAGCATGTGGTGTTATTGG    543
```

 gi|2708805|gb|AF037359.1|AF037359 Paulownia kawakamii superoxide dismutase (SOD5) mRNA, complete cds
Length=794

Score = 276 bits (139), Expect = 6e-71
Identities = 352/423 (83%), Gaps = 0/423 (0%)
Strand=Plus/Plus

```
Query    30   CAGTGAGGGTGTTGCTGGAACTATCCTCTTTACCCAAGAGGGAGATGGCCCAACTACTGT  89
              ||||||||||||| || ||| |||  ||| |||| ||||| ||||||| ||| |||| |||
Sbjct    117  CAGTGAGGGTGTTAGTGGCACCATCTACTTCACCCAGGAAGGAGATGGTCCAACAACTGT  176

Query    90   CACCCGAAACATTTCTCGCCCTCAACCCTCGGCTTCATCGTTTCCATCTTCATCCTCTTCG  149
              ||  ||||| |||||||||  |||| ||| |  || || ||||  ||||| |||||||||
Sbjct    177  TACTGGAAACGTTTCTGGCCTTAAGCCTGGACCCCATGGCTTTCATGTGCATGCCCTTGG  236

Query    150  GGACACAACCAATGGTTGCATGTCAACTGGACCACATTTCAATCCTGCTGGCAAAGAGCA  209
              |||||  |||||||| | ||||| ||||||||| || ||||||||||||||||||||||
Sbjct    237  TGACACCACCAATGGTTGTTTGTCAACTGGACCTCACTTCAATCCTGCTGGCAAAGAGCA  296

Query    210  TGGGTCTCCTGAAGATGAGACTCGTCATGCTGGTGATCTTGGAAATATCACTGTTGGGGA  269
              |||  ||||||| ||||||   | ||||||||||||| |||||| ||| || || ||| ||
Sbjct    297  TGGAGCTCCTGATGATGAGGTTCGCCATGCTGGTGACCTTGGGAATGTCACAGTTGGAGA  356

Query    270  TGACGGAACTGCTTGCTTCACAATTGTTGACAAACAGATTCCTCTCACTGGACCACACTC  329
              || || |||||  ||||||||| ||||| |||| || |||| || || || |||||| ||
Sbjct    357  AGATGGCACTGCTGCTTTCACTATTGTTGACAAGCAGATACCACTTACAGGACCACATTC  416

Query    330  TATCATTGGTAGGGCTGTTGTTGTCCATGCAGATCCTGATGACCTTGGCAAGGGTGGACA  389
              |||  || |||||  |||| |||||| || || | ||||||||||||||||||||||||
Sbjct    417  CATAATTGGAAGAGCTGTAGTTGTTCATGCTGATCCTGATGATCTTGGAAAGGGTGGACA  476

Query    390  TGAGCTTAGCAAATCCACTGGAAATGCTGGTGGCAGGATAGCTTGTGGTATTATTGGCCT  449
              ||| ||  |||||  ||||||||||||||||||| ||   | |||||||||| ||||||
Sbjct    477  TGAACTGAGCAAAACCACTGGAAATACTGGTGGAAGAGTTGCTTGTGGTATCAATGGCCT  536

Query    450  TCA    452
              |||
Sbjct    537  TCA    539
```

 gi|39840778|emb|AJ428575.2|OEU428575 Olea europaea Cu/Zn super-oxide dismutase (ole e 5 allergen)
Length=714

Fig 5 Continued

```
Score =  272 bits (137),  Expect = 9e-70
 Identities = 331/393 (84%),  Gaps = 2/393 (0%)
 Strand=Plus/Plus Query  61    ACCCAAGAGGGAGATGGCCCAACTACTGTGACCGGAAACATTTCTGGCCTCAAGCCTGGG  120
             ||||||||| ||||||||| |||||||||||| || |||||| ||||||||| ||||||||
Sbjct  61    ACCCAAGAAGGAGATGGTCCAACTACTGTTACTGGAAACCTTTCTGGCCTTAAGCCTGGA  120

Query  121   CTTCATGGTTTCCATGTTCATGCTCTTGGGGACACAACCAATGGTTGCATGTCAACTGGA  180
             |||||||| || |||||| || || ||||| ||||| |||||||| || ||||||||||||
Sbjct  121   CTTCATGGCTTTCATGTCCACGCCCTGGTGACACCACCAATGGCTGTATGTCAACTGGA  180

Query  181   CCACATTTCAATCCTGCTGGCAAAGAGCATGGGTCTCCTGAAGATGAGACTCGTCATGCT  240
             || |||||||||||| ||||| |||||||| |||| |||||||||| | ||||||||||||
Sbjct  181   CCTCATTTCAATCCTGTTGGGAAAGAGCATGGTGCACCTGGAGATGAGAACCGTCATGCT  240

Query  241   GGTGATCTTGGAAATATCACTGTTGGGGATGACGGAACTGCTTGCT-TCACAATTGTTGA  299
             ||||||||||| |||||||| ||||  || || || || ||  |||| |||| |||||||
Sbjct  241   GGTGATCTTGGTAATATCACAGTTGGCGAAGATGGCACCGC-TGCTATCAACATTGTTGA  299

Query  300   CAAACAGATTCCTCTCACTGGACCACACTCTATCATTGGTAGGGCTGTTGTTGTCCATGC  359
             ||| ||||| ||||| || |||||||| || || ||||| || || || |||||||| |
Sbjct  300   CAAGCAGATACCTCTTACAGGACCACATTCCATAATTGGAAGAGCAGTAGTTGTCCATTC  359

Query  360   AGATCCTGATGACCTTGGCAAGGGTGGACATGAGCTTAGCAAATCCACTGGAAATGCTGG  419
             |||||||||| |||| || ||||| |||| ||||| |||||   ||||||||||||||||
Sbjct  360   AGATCCTGATGATCTTGGAAGGGGTGGTCATGAACTGAGCAAGAGCACTGGAAATGCTGG  419

Query  420   TGGCAGGATAGCTTGTGGTATTATTGGCCTTCA  452
             ||| ||  | |||||||||||| ||||||||||
Sbjct  420   TGGAAGAGTTGCTTGTGGTATCATTGGCCTTCA  452
```

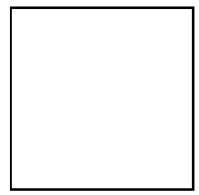

>gi|13751865|gb|AF355460.1|AF355460 Solanum tuberosum Cu/Zn-superoxide dismutase mRNA, partial cds
Length=617

```
Score =  268 bits (135),  Expect = 1e-68
 Identities = 330/395 (83%),  Gaps = 0/395 (0%)
 Strand=Plus/Plus Query  52    ATCCTCTTTACCCAAGAGGGAGATGGCCCAACTACTGTGACCGGAAACATTTCTGGCCTC  111
             |||||||| || ||||| ||||||| ||||| |||||| ||  |  |||||||||||||
Sbjct  30    ATCCTCTTCACTCAAGATGGAGATGCTCCAACCACAGTTAATGGAAATATTTCTGGCCTA  89

Query  112   AAGCCTGGGCTTCATGGTTTCCATGTTCATGCTCTTGGGGACACAACCAATGGTTGCATG  171
             || ||||| ||||||||| ||||||||||| ||||| || || |||| |||| ||||||
Sbjct  90    AAACCTGGACTTCATGGCTTCCATGTCCATGCCCTTGGTGATACCACAAATGGCTGCATG  149

Query  172   TCAACTGGACCACATTTCAATCCTGCTGGCAAAGAGCATGGGTCTCCTGAAGATGAGACT  231
             ||||| |||||||||| |||||||||||| | |||||||| || ||||||||||||  |
Sbjct  150   TCAACAGGACCACATTACAATCCTGCTGGTAAGGAGCATGGTGCTCCTGAAGATGAGGTG  209

Query  232   CGTCATGCTGGTGATCTTGGAAATATCACTGTTGGGGATGACGGAACTGCTTGCTTCACA  291
             |||||||||||||||||||| ||| ||||||| || |||| || || |||||| |  ||
Sbjct  210   CGTCATGCTGGTGATCTTGGTAACATCACAGTTGGAGAAGATGGTACTGCATCTTTTACT  269

Query  292   ATTGTTGACAAACAGATTCCTCTCACTGGACCACACTCTATCATTGGTAGGGCTGTTGTT  351
             |||   |||||||||||||||||||||| || || ||||||| || |||||||||||||
Sbjct  270   ATTACCGACAAGCAGATTCCTCTCACTGGTTCACAATCCATCATTGGAAGAGCTGTTGTT  329

Query  352   GTCCATGCAGATCCTGATGACCTTGGCAAGGGTGGACATGAGCTTAGCAAATCCACTGGA  411
```

Fig 5 Continued

```
             || ||||| |||||||||||| ||||| ||||| |||||||||||| || |||  |||||||
Sbjct  330   GTTCATGCTGATCCTGATGATCTTGGAAAGGGAGGACATGAGCTCAGTAAAAGCACTGGA   389

Query  412   AATGCTGGTGGCAGGATAGCTTGTGGTATTATTGG   446
             |||||||| || ||||| ||||||||||||||||
Sbjct  390   AATGCTGGCGGAAGGATTGCTTGTGGTATTATTGG   424
```

Fig 6: Detail of SEQ ID No. 1

Organization Applicant
----------------------

Street : Rafi marg,

City : New Delhi

State : Delhi

Country : India

PostalCode : -110001

PhoneNumber :

FaxNumber :

EmailAddress :

<110> OrganizationName : COUNCIL OF SCIENTIFIC & INDUSTRIAL RESEARCH

Application Project
-------------------

<120> Title : SUPEROXIDE DISMUTASE (SOD) GENE AND A METHOD OF IDENTIFYING AND
    CLONING THEREOF <130> AppFileReference : 0038NF2006

<140> CurrentAppNumber :

<141> CurrentFilingDate : 2006-03-31

Sequence
--------

<213> OrganismName : Potentilla atrosanguinea

Fig 6 Continued

<400> PreSequenceString :

MAKGVAVLSS SEGVAGTILF TQEGDGPTTV TGNISGLKPG LHGFHVHALG DTTNGCMSTG 60

PHFNPAGKEH GSPEDETRHA GDLGNITVGD DGTACFTIVD KQIPLTGPHS IIGRAVVVHA 120

DPDDLGKGGH ELSKSTGNAG GRIACGIIGL QG 152

<212> Type : PRT

<211> Length : 152

SequenceName : Polypeptide sequence of SOD gene SEQ ID NO. 1

SequenceDescription :

Fig 7: Detail of SEQ ID No. 2

Organization Applicant

----------------------

Street : Rafi marg,

City : New Delhi

State : Delhi

Country : India

PostalCode : -110001

PhoneNumber :

FaxNumber :

EmailAddress :

<110> OrganizationName : COUNCIL OF SCIENTIFIC & INDUSTRIAL RESEARCH

Application Project

-------------------

<120> Title : SUPEROXIDE DISMUTASE (SOD) GENE AND A METHOD OF IDENTIFYING AND
    CLONING THEREOF <130> AppFileReference : 0038NF2006

<140> CurrentAppNumber :

<141> CurrentFilingDate : 2006-03-31

Sequence

--------

<213> OrganismName : Potentilla atrosanguinea

<400> PreSequenceString :

acgggggggg gactgaaata aatagagagg gtcatagtca catttgcatt taggtatctg    60

Fig 7 Continued attccattca caaacctcca actcccacct ctctctctat ttctcttcat cttcatcatc    120
ttagggtgca ctgagatcac tttgaaacat ggcaaagggc gttgctgtac ttagctccag    180
tgagggtgtt gctggaacta tcctctttac ccaagaggga gatggcccaa ctactgtgac    240
cggaaacatt tctggcctca agcctgggct tcatggtttc catgttcatg ctcttgggga    300
cacaaccaat ggttgcatgt caactggacc acatttcaat cctgctggca aagagcatgg    360
gtctcctgaa gatgagactc gtcatgctgg tgatcttgga aatatcactg ttggggatga    420
cggaactgct tgcttcacaa ttgttgacaa acagattcct ctcactggac cacactctat    480
cattggtagg gctgttgttg tccatgcaga tcctgatgac cttggcaagg gtggacatga    540
gcttagcaaa tccactggaa atgctggtgg caggatagct tgtggtatta ttggccttca    600
aggatgaact ggaccaggga gcgaaacaca ggcatcttgt tgaattaaaa cttgagatat    660
tagcgaactc ttcggaattg agtattgaaa caaggaatac atttgtcatt accaatacgt    720
ttggcttaga cctgtattct gtatctcaat agttttctgt gtggttgttt gacagttatt    780
tgtgctcagg ctatttcaaa gggataaaca cagtaacttt cttgctttga caaaaaaaaa    840
aaaaaaaaaa aaaaaa                                                   856

<212> Type : DNA

<211> Length : 856

SequenceName : Full length cDNA SOD gene of SEQ ID No. 2

SequenceDescription :

Fig 8: detail of SEQ ID No. 3

Organization Applicant

----------------------

Street : Rafi marg,

City : New Delhi

State : Delhi

Country : India

PostalCode : -110001

PhoneNumber :

FaxNumber :

EmailAddress :

<110> OrganizationName : COUNCIL OF SCIENTIFIC & INDUSTRIAL RESEARCH

Application Project

-------------------

<120> Title : SUPEROXIDE DISMUTASE (SOD) GENE AND A METHOD OF IDENTIFYING AND
    CLONING THEREOF <130> AppFileReference : 0038NF2006

<140> CurrentAppNumber :

<141> CurrentFilingDate : 2006-03-31

Sequence

--------

<213> OrganismName : Potentilla atrosanguinea

<400> PreSequenceString :

atggcaaagg gcgttgctgt acttagctcc agtgagggtg ttgctggaac tatcctcttt    60

Fig 8 Continued acccaagagg gagatggccc aactactgtg accggaaaca tttctggcct caagcctggg    120
cttcatggtt tccatgttca tgctcttggg gacacaacca atggttgcat gtcaactgga    180
ccacatttca atcctgctgg caaagagcat gggtctcctg aagatgagac tcgtcatgct    240
ggtgatcttg gaaatatcac tgttggggat gacggaactg cttgcttcac aattgttgac    300
aaacagattc ctctcactgg accacactct atcattggta gggctgttgt tgtccatgca    360
gatcctgatg accttggcaa gggtggacat gagcttagca aatccactgg aaatgctggt    420
ggcaggatag cttgtggtat tattggcctt caaggatga                          459

<212> Type : DNA

<211> Length : 459

SequenceName : Coding sequence of potentialla SOD gene of SEQ ID NO. 3

SequenceDescription :

Fig 9: Detail of SEQ ID No. 4

Organization Applicant

----------------------

Street : Rafi marg,

City : New Delhi

State : Delhi

Country : India

PostalCode : -110001

PhoneNumber :

FaxNumber :

EmailAddress :

<110> OrganizationName : COUNCIL OF SCIENTIFIC & INDUSTRIAL RESEARCH

Application Project

-------------------

<120> Title : SUPEROXIDE DISMUTASE (SOD) GENE AND A METHOD OF IDENTIFYING AND
    CLONING THEREOF <130> AppFileReference : 0038NF2006

<140> CurrentAppNumber :

<141> CurrentFilingDate : 2006-03-31

Sequence

--------

<213> OrganismName : Potentilla atrosanguinea

<400> PreSequenceString :

caagagggag atggcccaac tactgtgacc ggaaacattt ctggcctcaa gcctgggctt    60

Fig 9 Continued catggtttcc atgttcatgc tcttggggac acaaccaatg gttgcatgtc aactggacca    120
catttcaatc ctgctggcaa agagcatggg tctcctgaag atgagactcg tcatgctggt    180
gatcttggaa atatcactgt tggggatgac ggaactgctt gcttcacaat tgttgacaaa    240
cagattcctc tcactggacc acactctatc attggtaggg ctgttgttgt ccatgcagat    300
cctgatgacc ttggcaaggg tggacatgag cttagcaaat ccactggaaa tgctggtggc    360
aggat    365

<212> Type : DNA

<211> Length : 365

SequenceName : Positive cDNA clone of SEQ ID No. 4

SequenceDescription :

Fig 10: Detail of SEQ ID No. 4

Organization Applicant
----------------------

Street : Rafi marg,

City : New Delhi

State : Delhi

Country : India

PostalCode : -110001

PhoneNumber :

FaxNumber :

EmailAddress :

<110> OrganizationName : COUNCIL OF SCIENTIFIC & INDUSTRIAL RESEARCH

Application Project
-------------------

<120> Title : SUPEROXIDE DISMUTASE (SOD) GENE AND A METHOD OF IDENTIFYING AND
    CLONING THEREOF <130> AppFileReference : 0038NF2006

<140> CurrentAppNumber :

<141> CurrentFilingDate : 2006-03-31

Sequence
--------

<213> OrganismName : Potentilla atrosanguinea

<400> PreSequenceString :

atggcaaagg gcgttgctgt actt

Fig 10 Continued

<212> Type : DNA

<211> Length : 24

SequenceName : Primer Sequence SEQ ID No. 5(a) Forward Primer

SequenceDescription :

Sequence

--------

<213> OrganismName : Potentilla atrosanguinea

<400> PreSequenceString :

tcatccttga aggccaataa tacca                    25

<212> Type : DNA

<211> Length : 25

SequenceName : Primer sequence SEQ ID No. 5(b) : Reverse primer

SequenceDescription :

Fig 11: SEQ ID No. 6

Organization Applicant

----------------------

Street : Rafi marg,

City : New Delhi

State : Delhi

Country : India

PostalCode : -110001

PhoneNumber :

FaxNumber :

EmailAddress :

<110> OrganizationName : COUNCIL OF SCIENTIFIC & INDUSTRIAL RESEARCH

Application Project

-------------------

<120> Title : SUPEROXIDE DISMUTASE (SOD) GENE AND A METHOD OF IDENTIFYING AND
    CLONING THEREOF <130> AppFileReference : 0038NF2006

<140> CurrentAppNumber :

<141> CurrentFilingDate : 2006-03-31

Sequence

--------

<213> OrganismName : Potentilla atrosanguinea

<400> PreSequenceString :

ccagtggatt tgctaagctc atgtcca               27

<212> Type : DNA

Fig 11 Continued

<211> Length : 27

SequenceName : Primer Sequence of SEQ ID No. 6(a) GSP1:Forward primer

SequenceDescription :

Sequence

--------

<213> OrganismName : Potentilla atrosanguinea

<400> PreSequenceString :

gtcatcaggg tctgcatgga caacaac                              27

<212> Type : DNA

<211> Length : 27

SequenceName : Primer sequence of SEQ ID No. 6(b) NES1: Reverse Primer

SequenceDescription :

Sequence

--------

<213> OrganismName : Potentilla atrosanguinea

<400> PreSequenceString :

atggttgcat gtcaactgga ccacatt                              27

<212> Type : DNA

<211> Length : 27

SequenceName : Primer Sequence of SEQ ID No. 6(c) GSP2: Forward Primer

SequenceDescription :

Sequence

--------

<213> OrganismName : Potentilla atrosanguinea

<400> PreSequenceString :

ttgcatgtca actggaccac atttcaa                              27

<212> Type : DNA

Fig 11 Continued

<211> Length : 27

SequenceName : Primer sequence of SEQ ID No. 6(d) NES2: Reverse Primer

SequenceDescription :

Sequence

--------

<213> OrganismName : Potentilla atrosanguinea

<400> PreSequenceString :

aagcagtggt atcaacgcag agtacgcggg                    30

<212> Type : DNA

<211> Length : 30

SequenceName : Primer Sequence of SEQ ID No. 6(e): SMART II A Oligonucleotide

SequenceDescription :

Sequence

--------

<213> OrganismName : Potentilla atrosanguinea

<400> PreSequenceString :

aagcagtggt atcaacgcag agtactnn                      28

<212> Type : DNA

<211> Length : 28

SequenceName : Primer sequence of SEQ ID No. 6(f): 3`- RACE CDS Primer A (3`-CDS):

SequenceDescription :

SUPEROXIDE DISMUTASE (SOD) GENE AND A METHOD OF IDENTIFYING AND CLONING THEREOF

CROSS-REFERENCE TO RELATED APPLICATIONS

This application is a divisional of U.S. patent application Ser. No. 11/499,505, filed Aug. 4, 2006, which claims benefit of Indian application 0928/DEL/2006, filed Mar. 31, 2006. The contents of each of these applications are incorporated herein by reference in their entirety.

FIELD OF INVENTION

The present invention relates to a Superoxide dismutase (SOD). Superoxide dismutase (SOD) cDNA of SEQ ID No. 2 obtained from *Potentilla atrosanguinea* containing coding gene sequence of SEQ ID No. 3 which codes for a polypeptide of SEQ ID No. 1 having Superoxide dismutase enzyme activity.

Further, it also relates to a set of primers useful for the amplification of Superoxide dismutase (SOD) gene coding cDNA of SEQ ID No. 3, wherein

```
                                      (SEQ ID NO: 5)
Forward primer    5'-ATGGCAAAGGGCGTTGCTGTACTT-3'
and;

(SEQ ID NO: 6)
Reverse primer    5'-TCATCCTTGAAGGCCAATAATACCA-3'
```

More particularly, it relates to a method of identifying and cloning of Superoxide dismutase (SOD) gene of SEQ ID NO 3, which on expression gives a Superoxide dismutase enzyme (EC 1.15.1.1) with the characteristics disclose in U.S. Pat. No. 6,485,950.

BACKGROUND AND PRIOR ART REFERENCES TO THE INVENTION

SOD is a ubiquitous enzyme present in plants, animals and microbes, which protects them against oxidative damage caused by superoxide radical (hereinafter, referred to $O_2^-$). The enzyme dismutates superoxide radical into hydrogen peroxide and oxygen as per the following redox reaction:

$$2O_2^- + 2H^+ = H_2O_2 + O_2$$

Thus, SOD has implications in all those reactions, wherein $O_2^-$ is produced in the amount leading to cellular injury.

According to the U.S. Pat. No. 6,485,950, we have extracted an autoclavable superoxide dismutase from *Potentilla* that could be autoclaved and shows activity at sub-zero temperature. Due to prevalence of *Potentilla* at difficult to access location of high altitude, and industrial implications of SOD as mentioned in our U.S. Pat. No. 6,485,950, it was essential to develop a system for the production of SOD of *Potentilla* in *E. coli* so as to obtain the SOD when desired.

Below is given state of the art knowledge in relation to isolation of SOD genes from various sources and their expression in *E. coli*, to produce SOD in recoverable quantities.

Reference may be made to document (1) by Wang, Z., He, Z., Shen, Q., Gu, Y., Li, S, and Yuan, Q. (J. of Chromatography B, 2005. 826: 114-121) wherein Cu/Zn SOD gene from *Cordyceps militaris* was overexpressed in *E. coli*.

Yet another reference may be made to document (2) by Liu, W., Zhu, R. H., Li, G. P., and Wang, D. C. (Protein Expr. Purif. 2002. 25: 379-388) wherein production of high yield of recombinant duck Cu/Zn SOD was achieved in *E. coli*.

Reference may be made to yet another document (3) by Pan, S. M., Hwang, G. B., and Liu, H. C. (Bot. Bull. Acad. Sin. 1999. 40: 275-281) wherein over-expression and characterization of cytosolic Cu/Zn SOD from rice in *E. coli* was achieved.

Reference may be made to document (4) by Hartman, J. R., Geller, T., Yavin, Z., Bartfeld, D., Kanner, D., Aviv, H., and Gorecki, M. (Proc. Natl. Acad. Sci. USA. 1986. 83: 7142-7146) wherein high-level expression of enzymatically active human Cu/Zn SOD was reported in *E. coli*.

Reference may be made to document (5) by Ken, C. F., Lin, C. T., Shaw, J. F., and Wu, J. L. (Marine Biotech. 2003. 5: 167-173) wherein the Cu/Zn SOD from zebrafish was overexpressed in *E. coli* and the active enzyme was purified.

Reference may be made to document (6) by Kim, T. S., Jung, Y., Na, B. K., Kim, K. S., and Chung, P. R. (Infect. Immun. 2000. 68: 3941-3948) wherein the Cu/Zn SOD gene from Faciola hepatica was cloned and expressed in *E. coli*.

The drawbacks are:
1. There is no SOD gene that is isolated from *Potentilla*, a source of Cu/ZnSOD that is autoclavable and functions at sub-zero temperature.
2. There is no SOD gene that is isolated from *Potentilla* and made to express in *E. coli*.
3. There is no SOD gene that is made to express in *E. coli* leading to SOD protein that is shown to be autoclavable.
4. There is no SOD gene that is made to express in *E. coli* leading to SOD protein that is shown to function at sub-zero temperature.

Comparative Data of Present SOD with other Known SOD

| Present invention | Prior art |
|---|---|
| The maximum thermostability of SOD described so far is at 80° C. | The maximum thermostability of SOD is 37° C. to 50° C. reference from Bueno P., Verla, J., Gallego, G. G., and Rio del A. L. (Plant Physiol. 1995. 108: 1151-1160) wherein the thermostability of Cu/Zn SOD isolated from the cotyledon of water melon has been shown, SOD activity reduced: (a) by 40% after 4 hour of incubation at 50.° C.; (b) by 50% after 15 minute of incubation at 70° C.; (c) by 80% after 60 minute of incubation |

-continued

| Present invention | Prior art |
|---|---|
| | at 80° C.; and (d) by 100% after 15 minute of incubation at 100° C. Reference may be made to Document by Miyata, K., Maejima, K., and Tomoda, K. (U.S. Pat. No. 4,563,349; Jan. 7, 1986) wherein SOD has been reported from a microorganism belonging to genus *Serratia* having the thermostability characters as follows: (a) Stable at 37° C. for 60 minutes; Inactivated by 50% when incubated at 50-60° C. for 60 minutes; and Inactivated by 100% when incubated at 80° C. for 5 minutes. |
| stability without adding an external stabilizer [the addition of hydrogen peroxide trapping agent, polyols, and sugars etc. are required to stabilise the enzyme from other sources such as germinated plant seeds | External stabilizer is required to enhance the stability of the product contains this enzyme. Reported SODs do not retain their activity at ambient temperature unless stabilized by the addition of polyols, sugars or any other stabilizing agent (Bresson-Rival; Delphine; Boivin; Patrick; Linden; Guy; Perrier; Erric; Humbert; Gerard; 1999; U.S. Pat. No. |
| Wide range of temperature functionality from sub-zero to above 50. degree. C. temperature which would immensely enhance the utility of the enzyme and its products and be safer for use for humans. | Temperature range for SOD activity has been reported between 5 to 45. degree. C. Hakam, N. and Simon, J. P. 1996. Physiol. Plant. 97: 209-216). However, thermostability and lower temperature for catalyzing dismutation of O.sub.2.sup.-. are not reported for the same enzyme. |
| Present enzyme is autoclavable. When SOD is to be injected in the body, a sterile composition would be needed and for that an autoclavable SOD would be an ideal one. Moreover, in reperfusion applications and storage of organs at low temperature, an autoclavable SOD would be required which can function efficiently at low temperature as well. Apart from the use of autoclaved SOD in pharmaceuticals and medical fields, sterile SOD will also be a choice in the cosmetic and food industry. | There is no report for autoclavable SOD. |

OBJECTS OF THE INVENTION

The main object of the invention is to provide a superoxide dismutase (SOD) Superoxide dismutase (SOD) cDNA of SEQ ID No. 2 obtained from *Potentilla atrosanguinea* containing coding gene sequence of SEQ ID No. 3 which codes for a polypeptide of SEQ ID No. 1 having Superoxide dismutase enzyme activity Another object of the present invention is to provide a set of primers useful for the amplification of Superoxide dismutase (SOD) gene coding cDNA of SEQ ID No. 3, wherein

```
                                            (SEQ ID NO: 5)
Forward primer    5'-ATGGCAAAGGGCGTTGCTGTACTT-3'
and;

(SEQ ID NO: 6)
Reverse primer    5'-TCATCCTTGAAGGCCAATAATACCA-3'
```

Further, another object of the present invention is to provide a method of identifying and cloning of superoxide dismutase (SOD) gene of SEQ ID NO 3, which on expression gives a superoxide dismutase enzyme (EC 1.15.1.1) with the characteristics disclose in U.S. Pat. No. 6,485,950.

Yet another object of the present invention is to provide a gene responsible for autoclavable superoxide dismutase from *Potentilla*.

Still another object of the present invention is to provide a gene responsible for autoclavable superoxide dismutase from *Potentilla* that is also functional at sub-zero temperature.

Still another object of the present invention is to provide a recombinant gene of SOD, which shows activity upon autoclaving and also shows activity at low temperature, in a plasmid vector leading to a new vector which carries the nucleotide sequence synthesizing the said SOD.

Still another object of the present invention is to transform bacterial host *E. coli* with the above said recombinant plasmid vector for expression of the SOD gene in the bacterial host.

BRIEF DESCRIPTION OF FIGURES

FIG. 2 represents comparison of the nucleotide sequence of the *Potentilla* Cu/Zn SOD with sequences from other plant species. Regions of complete homology are indicated with asterisks (SEQ ID NOS 24, 3 & 25-28 are disclosed respectively in order of appearance).

FIG. 3 represents comparison of the deduced amino acid sequence of the *Potentilla* Cu/Zn SOD with sequences from other plant species. Regions of complete homology are indicated with asterisks (SEQ ID NOS 29, 1 & 30-36 are disclosed respectively in order of appearance).

FIG. 4 (A) represents expression and purification of *Potentilla* SOD in *E. coli*. C, Control; I, Protein induced by IPTG; P, Purified SOD. The gel was stained by silver staining. (B). Activity staining of the gel to depict the activity of purified SOD. P, Purified SOD.

FIG. 5 represents the result of alignment of present sod gene with the sod gene of other plant species (SEQ ID NOS 37-72 are disclosed respectively in order of appearance)

FIG. 6 represents the details of Polypeptide sequence of SOD gene SEQ ID NO. 1.

FIG. 7 represents the details of full length cDNA SOD gene of SEQ ID No. 2

FIG. 8 represents the details of coding sequence of *potentialla* SOD gene of SEQ ID NO. 3

FIG. 9 represents the details of positive cDNA clone of SEQ ID No. 4

FIG. 10 represents primer Sequence (SEQ ID NO: 5) Forward Primer and Primer sequence (SEQ ID NO: 6): Reverse primer.

FIG. 11 represents Details of primers used for RACE (a) Primer Sequence of (SEQ ID NO. 7) GSP1:Forward primer.

Figure 1:
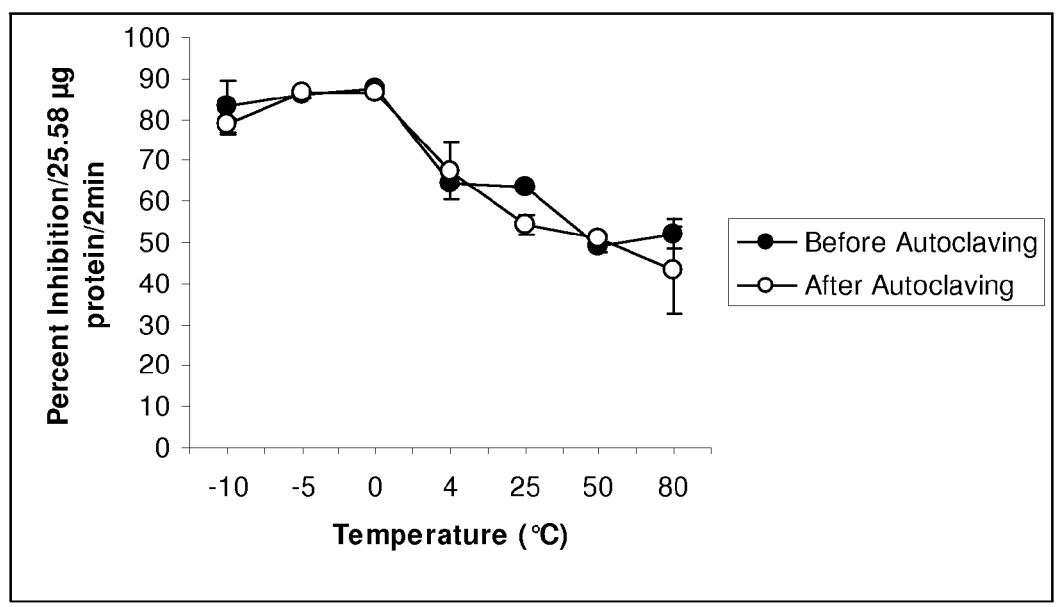
FIG. 1 represents effect of assay temperature on SOD activity. *Potentilla* SOD expressing in *E. coli* was purified and assayed before and after autoclaving at different temperatures.

(b) Primer sequence of (SEQ ID NO. 8) NES1: Reverse Primer (c) Primer Sequence of (SEQ ID NO. 9) GSP2: Forward Primer (d) Primer sequence of (SEQ ID NO. 10) NES2: Reverse Primer.

(Also disclosed are SEQ ID NOS 11 & 12 respectively in order of appearance).

SUMMARY OF THE INVENTION

The present invention provides superoxide dismutase gene from *Potentilla atrosanguinea* and its expression in heterologous system and comprises of a construct which carries the coding nucleotide sequence of SEQ ID 3 which is responsible fore synthesis of said SOD and transformed *E. coli* producing the SOD protein. This SOD protein is autoclavable and also functions at sub-zero temperature.

DETAILED DESCRIPTION OF THE INVENTION

Accordingly, the present invention provides a superoxide dismutase (SOD) cDNA of SEQ ID No. 2 obtained from *Potentilla atrosanguinea*, wherein the said cDNA comprises 856 nucleotide bases.

In an embodiment of the present invention, the said cDNA has entire coding sequence along with pre- and post-coding sequences.

The present invention also provides a superoxide dismutase (SOD) gene coding cDNA of SEQ ID No. 3, wherein the said coding cDNA comprises 459 nucleotide bases.

Further, it also provides a superoxide dismutase (SOD) polypeptide of SEQ ID No. 1, wherein the said polypeptide comprises 152 amino acids.

In an embodiment of the present invention, the said polypeptide is autoclavable.

In another embodiment of the present invention, the said polypeptide is functional at temperature range of <–10° C. to +80° C.

The present invention further provides a set of primers useful for the amplification of Superoxide dismutase (SOD) gene coding cDNA of SEQ ID No. 3, wherein

```
                                           (SEQ ID NO: 5)
Forward primer   5'-ATGGCAAAGGGCGTTGCTGTACTT-3'
and;

(SEQ ID NO: 6)
Reverse primer   5'-TCATCCTTGAAGGCCAATAATACCA-3'
```

1. Further, it provides A method of identifying and cloning of superoxide dismutase (SOD) gene of SEQ ID NO 3 which codes for a polypeptide of SEQ ID No. 1 having Superoxide dismutase enzyme activity, wherein the said method comprising the steps of:

a) isolating the mRNA from leaves of *potentialla*;

b) synthesizing the cDNA from mRNA as obtained from step (a);

c) constructing a cDNA library of the DNA of *potentialla* followed by the cloning of the cDNA obtained from step (b) in a suitable vector preferably in bacteriophage;

d) screening the said library obtained from step (c) followed by the primary, secondary and tertiary screening for identification of positive cDNA clones;

e) isolating the DNA from positive cDNA clones obtained from step (d);

f) amplifying the said DNA using the primers comprising:

```
                                          (SEQ ID NO: 13)
Forward Primer:   5'-GTTGTAAAACGACGTGCCAGT-3'

(SEQ ID NO: 14)
Reverse Primer:   5'-CACAGGAAACAGCTATGACC-3';
``` g) amplifying the ends of cDNA obtained from step (e) through rapid amplification of cDNA ends technique (RACE) using two set of primers to get the full length desired Superoxide dismutase (SOD) DNA of SEQ ID NO. 2 wherein the said primers comprising:

```
                                           (SEQ ID NO: 7)
Forward Primer:   5'-CCAGTGGATTTGCTAAGCTCATGTCCA-3'

(SEQ ID NO: 8)
Reverse Primer:   5'-GTCATCAGGGTCTGCATGGACAACAAC-3'

(SEQ ID NO: 9)
Forward Primer:   5'-ATGGTTGCATGTCAACTGGACCACATT-3'

(SEQ ID NO: 10)
Reverse Primer:   5'-TTGCATGTCAACTGGACCACATTTCAA-3'
``` g) amplifying the ends of cDNA obtained from step (e) through rapid amplification of cDNA ends technique (RACE) using different set of primers to get the full length desired Superoxide dismutase (SOD) DNA of SEQ ID NO. 2 wherein the said primers comprising:

```
                                           (SEQ ID NO: 7)
Forward Primer (GSP1):
5'-CCAGTGGATTTGCTAAGCTCATGTCCA-3'
```

```
                                           (SEQ ID NO: 8)
Reverse Primer (NES1):
5'-GTCATCAGGGTCTGCATGGACAACAAC-3'

(SEQ ID NO: 9)
Forward Primer (GSP2):
5'-ATGGTTGCATGTCAACTGGACCACATT-3'

(SEQ ID NO: 10)
Reverse Primer (NES2):
5'-TTGCATGTCAACTGGACCACATTTCAA-3'

(SEQ ID NO: 11)
SMART II A Oligonucleotide:
5'AAGCAGTGGTATCAACGCAGAGTACGCGGG-3'

(SEQ ID NO: 73)
3'-RACE CDS Primer A (3'-CDS):
5'AAGCAGTGGTATCAACGCAGAGTAC(T)$_{30}$N$_{-1}$N-3'

(SEQ ID NO: 15)
5'-RACE CDS Primer (5'-CDS)
5'-(T)$_{25}$N$_{-1}$N-3'

(SEQ ID NO: 16)
Universel Primer Mix A (UPM): Long:
5'TAATACGACTCACTATAGGGCAAGCAGTG
GTATCAACGCAGAGT-3'

(SEQ ID NO: 17)
Universel Primer Mix A (UPM): Short:
5'-CTAATACGACTCACTATAGGGC-3'

(SEQ ID NO: 23)
Nested Universel Primer A (NUP):
5'-AAGCAGTGGTATCAACGCAGAGT-3'
``` h) amplifying the coding sequence of Superoxide dismutase (SOD) of SEQ ID No. 3 using a set of primers designed from start and stop codon of full length desired Superoxide dismutase (SOD) DNA of SEQ ID NO. 2 wherein the said primers have the following sequences:

```
                                           (SEQ ID NO: 5)
Forward Primer:    5'-ATGGCAAAGGGCGTTGCTGTACTT-3'

(SEQ ID NO: 6)
Reverse Primer:    5'-TCATCCTTGAAGGCCAATAATACCA-3'
``` i) cloning the amplified product obtained from step (g) into pQE 30 expression vector followed by the transformation it into competent *E. coli* cells to get an expression construct;

j) isolating the plasmid DNA by conventional method followed by sequencing to confirm the said SOD gene.

In an embodiment of the present invention, the polyclonal antibodies were raised against the purified SOD and used for cDNA library screening synthesized from young leaf mRNA.

In another embodiment of the present invention, library was screened and positive cDNA clones were amplified by polymerase chain reaction (hereinafter called as PCR) and two PCR products were obtained. These were sequenced and approximately 85% of the gene encoding SOD was obtained.

Further, in another embodiment of the present invention, the sequences of the said cDNA clones does not have the start and end codon and smaller by 21%.

In yet another embodiment of the present invention, primers were designed based on the sequences of positive cDNA clones and the rapid amplification of cDNA ends technique (hereinafter called as RACE) was employed to amplify the SOD full length gene.

In still another embodiment of the present invention, the said SOD gene is sequenced and analyzed comprising the sequences set forth in SEQ ID No. 2.

In still another embodiment of the present invention, the said full length SOD gene contains 856 nucleotide bases.

In still another embodiment of the present invention, the said full length SOD gene has entire coding sequence along with pre- and post-coding sequences.

In still another embodiment of the present invention, a set of primers are designed based on the full length SOD gene to amplify the superoxide dismutase (SOD) gene coding cDNA of SEQ ID No. 3.

In still another embodiment of the present invention, the said coding cDNA comprises 459 nucleotide bases.

In still another embodiment of the present invention, said SOD gene is ligated into a vector to yield a recombinant plasmid which upon transformation into a suitable *E. coli* host resulted into a clone.

In still another embodiment of the present invention, the said coding sequence of SOD gene of SEQ ID No. 3 corresponding to polynucleotides encoding Superoxide dismutase (SOD) enzyme.

Further, the present invention also provides an expression construct included sequences encoding a selectable marker and a terminator sequence.

In the present invention, leaves of *Potentilla* plant growing at Kunzum Pass (altitude 4517 m; 32° 24' N; 077° 38' E) in Lahaul and Spiti district of Himachal Pradesh in Western Himalaya of India were collected and stored in liquid nitrogen. We had earlier reported in our U.S. Pat. No. 6,485,950 that the leaves of this plant has SOD that is autoclavable and functions at sub-zero temperature. Thus the gene encoding such a SOD was identified, isolated and cloned in *E. coli* by techniques well known and routinely practiced in the art. The present SOD gene was sequenced and analyzed for its sense orientation, comprising the sequences set forth in SEQ ID No; 2. The term "sense" as used herein, refers to a substantial run of RNA bases having essentially the same bases as a specific RNA sequence (e.g., mRNA). The invention also embraced polynucleotides encoding the amino acid sequences set out in SEQ ID No. 1. The invention also provided host cells, comprising a polynucleotide of the invention in a manner that permits expression of the encoded SOD polypeptide. Suitable host cells for transformation with the SOD gene of the invention include bacterial cells e.g. *E. coli*. Polynucleotides of the invention may be introduced into the host cell as a part of a circular plasmid using the well known methods for introducing DNA into the host cell and routinely practiced in the art. Host cells of the invention are a valuable source for industrial scale production of recombinant SOD.

Polyclonal antibody, in the present invention refers to an antibody produced in the normal immune system in response to an antigen consists of a number of closely related, but not identical proteins).

Vector, in the present invention refers to the sequence of DNA capable of accepting foreign DNA and take the form of a circular plasmid DNA that shows resistance to a given antibiotic The gene sequence of the invention was compared with the SOD reported from other plants to figure out the uniqueness of the gene (FIG. 2). Sequences unique to the polypeptides of the invention are recognizable through sequence comparison to other known polypeptides, and can be identified through use of alignment programs routinely utilized in the art, e.g., those made available in public sequence databases (FIG. 3). This suggested that the sequence obtained were incomplete. SEQ ID No; 3 however, shared at least 80%, at least 82%, at least 83%, at least 85%, at least 86% sequence homology with SOD genes reported from other plants. Percent sequence "homology" with respect to polynucleotides of the invention is defined herein as the percentage of nucleotide bases in the candidate sequence that are identical to the nucleotides in the SOD coding sequence after aligning the sequences, if necessary, to achieve the maximum percent sequence identity.

It is cumulative effect/combination of amino acids for the entire 100% amino acid composition that this property is observed. This entire composition provides this protein the effect that protein has this effect.

The following examples are given by way of illustration of the present invention and should not be construed to limit the scope of the present invention.

EXAMPLE-1

Raising Antibodies Against SOD in Rabbit

Polyclonal antibodies against purified protein were raised in one-year-old male rabbit (New Zealand type). Purified SOD protein (100 µg in 500 µl of potassium phosphate buffer; pH, 7.0) was emulsified in 1 ml of Freund's complete adjuvant and administered intramuscularly using disposable syringe. Complete Freund's adjuvant was obtained from Bangalore Genei, India that contained paraffin oil, mannide monooleate as an emulsifier and heat killed *Mycobacterium tuberculosis*. After $7^{th}$ days of primary injection, a booster dose (1 ml, containing 60 µg of purified protein emulsified in 1 ml of incomplete adjuvant) was administered. Adjuvant (500 µl) was thoroughly emulsified with the purified enzyme (500 µl: 100 µg) to obtain a stable antigen-adjuvant emulsion by rapidly withdrawing and expelling the antigen-adjuvant mix using a 22 gauge needle fitted to a sterile syringe. Complete emulsification was tested by placing a drop of the mixture onto a still surface of distilled water. The intactness of the droplet assures complete mixing. Antigen-adjuvant mixture (800 µl) was injected in thigh muscles of rabbit using a 22 gauge needle. Blood was collected from heart of the rabbit and allowed to clot for 2 hours at room temperature. After overnight storage at 4° C., the edges of the clot were rimmed using a Pasture pipette and centrifuged at 150×g for 5 min. Supernatant was collected and centrifuged for 15 min at 350×g to remove cell debris. Sodium azide was added to a concentration of 0.025% and the serum was stored at 4° C. After second booster dose, a small amount of blood was collected to test for the presence of the antibody using Ouchterlony Double Diffusion (hereinafter known as ODD) as described by Kanematsu, S, and Asada, K. (1990) Plant Cell Physiol. 31: 99-112. Thus, in a 85 mm petri plate, 1.5% agar prepared in 0.15 M NaCl, 20 mM potassium phosphate of pH 7.0 and 0.02% sodium azide was poured to a thickness of 3 mm. Antigen (20 µl containing 4 µg of protein) and antibody were loaded into the 3 mm diameter well cut with the help of cork-borer. Petri plate was covered and kept in a humid environment for 16-24 hour at 37° C. and examined for line of immune precipitation.

EXAMPLE-2

RNA Isolation, Quantification of RNA, Gel-electrophoresis and Purification of Poly A$^+$ mRNA from Total RNA Ribonucleic acid (hereinafter known as, RNA) from young leaf tissue of *Potentilla* was isolated using the modified guanidine hydrochloride procedure (Lal. L., Sahoo. R., Gupta. R. K., Sharma. P. and kumar. S. Plant Molecular Biology Reporter 19: 181a-181f.). Leaf tissue (500 mg) was ground in liquid nitrogen to fine powder. Powder was transferred into a new mortar containing 5 ml of the GH buffer (8M guanidine hydrochloride, 20 mM EDTA, 20 mM MES, 100 mM βME) and was ground further. Resulting homogenate was transferred to an oak-ridge tube containing equal volume of phenol:chloroform:isoamylalcohal (25:24:1). Phases were emulsified by vortexing and separated by centrifugation at 10,000 rpm for 20 min (7° C.). Upper aqueous phase was transferred to a fresh oak-ridge tube and extracted with the equal volume of chloroform:isoamylalcohal (24:1). Resulting upper aqueous phase was transferred to a corex tube and RNA was precipitated by adding 0.2 volume of 1 M acetic acid and 0.7 volume of chilled ethanol. The tubes were kept at −72° C. for 3 h. Precipitate was pelleted by centrifugation at 10,000 rpm for 10 min at 4° C. Pellet was washed thrice using 5 ml of 3 M sodium acetate (pH 5.2) followed by final washing with 70% chilled ethanol. Pellet was dried and dissolved in minimum volume of DEPC-treated autoclaved water. RNA was quantified by measuring absorbance at 260 nm and the purity was monitored by calculating the ratio of absorbance measured at 260 and 280 nm. A value >1.8 at 260/280 nm was considered ideal for the purity of RNA used in the present investigation. The formula used to calculate RNA concentration and yield was as follows:

Concentration of RNA (µg/ml)=$A_{260}$ (absorbance at 260 nm)×40×dilution factor Total yield (µg)=concentration×volume of stock RNA sample To check the integrity of RNA, 5-6 µg of RNA in 4.5 µl of DEPC treated autoclaved water was diluted with 15.5 µl of M1 solution (2 µl of 5×MOPS buffer, 3.5 µl of formaldehyde, and 10 µl of formamide [5×MOPS buffer: 300 mM sodium acetate, 10 mM MOPS (3-{N-morpholino}propanesulfonic acid}, 0.5 mM ethylene diamine tetra-acetic acid (EDTA)] and incubated for 15 minutes at 65° C. RNA was loaded onto 1.0% formaldehyde agarose-gel after adding 2 µl of formaldehyde-gel loading buffer [50% glycerol, 1 mM EDTA (pH, 8.0), 0.25% bromophenol blue, 0.25% xylene cyanol FF], and electrophoresed at 72 volts in 1×MOPS buffer (60 mM sodium acetate, 2 mM MOPS, 0.1 mM EDTA), (Sambrook, J., Fritsch, E. F. and Maniatis, T. 1989. Molecular Cloning: A Laboratory Manual, Cold Spring Harbor Laboratory Press, Plainview, N.Y.).

Poly-A mRNA was purified from the total RNA using $dC_{10}T_{30}$ oligonucleotides attached covalently to polystyrene-latex particles (Oligotex™, Qiagen Inc). Oligotex selectively binds mRNA with poly-A tail to allow purification leaving all other RNA species that lack poly-A tail. 1 mg of total RNA was used as the starting material for the isolation of the mRNA and manufacturer's instructions were followed during the procedure.

EXAMPLE-3

Construction of a Directional Complementary DNA Library (Hereinafter Referred to cDNA Library)

Poly-A$^+$mRNA was used to synthesize cDNA using Time-Saver™ cDNA synthesis kit (Amersham Pharmacia Biotech. USA). First strand was synthesized using MMLV-reverse transcriptase in the presence of a bifunctional primer [5'd (AAC TGG AAG AAT TCG CGG CCG CAG GAA $T_{18}$)p 3](SEQ ID NO: 18) having an oligo (dT$_{18}$)SEQ ID NO: 19)

tract at the 3"-end of a restriction site for Not I. Second strand synthesis is initiated by DNA polymerase I after RNase H has nicked the RNA strand of the RNA:cDNA hybrid. The cDNA produced is extracted with phenol/chloroform and purified on a Sepharose CL-4B spun column. An Eco RI adaptor (5'-d [AATTCGGCACGAGG]-3' (SEQ ID NO: 20), [GCCGTGCTCC]p-5') (SEQ ID NO: 21) is ligated to other end of the cDNA. cDNA was digested with Not I to release site on oligo ($dT_{18}$-Not I) (SEQ ID NO: 19) primer. cDNA's with Eco RI and Not I overhangs were phosphorylated to disallow self-ligation but ligation to the dephosphorylated vector.

Bacteriophage λ vector (λ ExCell Not I/Eco RI/CIP) was selected for cloning of cDNA's with Eco RI and Not I overhang generated as above. λ ExCell is derived from a λ Charon vector engineered to contain an internal, linearized copy of pExCell. Following the construction and screening using the lawn cells (E. coli strain NM522), the bacteriophage containing the clone of interest were used to infect a special E. coli strain (NP66) that enables the in vivo release of pExCell, a circular, autonomously replicating pUC-based phagemid. In vivo excision of pExCell is accomplished by site-specific recombination between attL and attR sites that flank the phagemid within the λ ExCell DNA. NP66 carries the accessory proteins require for excision under the control of a thermo-inducible promoter. In vivo excision is accomplished by infection of NP66 with λ ExCell followed by growth at 39° C., which enables the expression of these accessory proteins.

The ligated vector and the cDNA fragments were packaged in an in vitro packaging system (Ready to Go Lambda packaging kit, Amersham Pharmacia Biotech. USA). In vitro packaging system for lambda DNA uses single lysogen, which codes for all necessary packaging proteins. The extract was prepared from E. coli lysogen in which the prophage carries a cos mutation. The cos mutation is a deletion in the cos site which prevents the endogenous prophage from being packaged; the exogenous recombinant DNA is, however, efficiently packaged. Packaging extracts also lack Eco K and other DNA restriction systems that recognize methylated DNA, which results in the efficient packaging of methylated and unmethylated cDNA.

EXAMPLE-4

Library Screening and Identification, Amplification and Purification of Positive Phage Library was screened using polyclonal antibodies raised against purified SOD as probe. Immobilized antibodies were detected using chemiluminescence based detection method (ECLT™ western blotting analysis system, Amersham Inc.). The library was plated by making the serial dilutions of packaging reaction in SM buffer (100 mM NaCl, 8 mM $MgSO_4$, 50 mM Tris-HCl and 0.01% gelatin). Autoclaved and dried nitrocellulose filter membranes fitting to the size of petri plate (82 mm) were used. Membranes were soaked in 10 mM isopropyl β-D-thiogalactopyranoside (hereinafter referred to IPTG) for 5 min, air-dried and used for screening. After 6 h incubation of the plated library or as the plaques started appearing, the plates were overlaid with IPTG-soaked nitrocellulose filters. The filters were overlaid by gently holding filters with blunt ended forceps at opposite edges and centering filter over plate, without trapping any air bubble. Filter was not moved once contact is made with the plate. The plates-filters (inverted) were incubated for another 4 h at 37° C. After incubation, the plates were marked with 18-gauge needle by puncturing asymmetrically for future alignment. Filters were removed from plates with protein side up. Positive plaques were selected using the correct orientation of the developed X-ray, filter and the plate. After marking plagues were cored out and placed in 300 μl of SM buffer for incubation at room temperature. After 2 h, it was centrifuged at 13,000×g for 10 min. The supernatant was collected in a fresh sterile tube followed by addition of 30 μl chloroform. The amplified phage was replated for secondary and tertiary screening. After tertiary screening the positive plaques were cored for in vivo phagemid release. For primary screening $10^5$ plaque forming unit (pfu) were taken and transferred to membrane. Membranes were hybridized with polyclonal antibody and developed as ECL instruction. Three strong positive clones were obtained and further taken for secondary screening which gave 70% positive signal. A few clones were taken for tertiary screening and this time all the clones gave 100% positive signal after tertiary screening. All the positive plaques were used to release the vector pExCell containing the cloned fragment.

EXAMPLE-5

In Vivo Release of Phagemid pExcell from Selected Clones

Host cells were prepared from released strain of E. coli NP66 in 2×YT medium (2×YT medium: 12 g trypton, 24 g yeast extract and 5 g glycerol in 1 liter of final volume in distilled/deionized water) containing 50 μg/ml spectinomycin, 30 μg/ml of chloramphenicol and 0.2% maltose. The culture was grown overnight at 32° C. 5 ml of 2×YT containing 50 μg/ml spectinomycin, 30 μg/ml of chloramphenicol and 0.2% maltose was incubated with 50 μl of the overnight culture. This culture was grown at 32° C. with shaking to an $A_{600}$ of 0.5-0.8. and cells were harvested by centrifugation at 3000×g. The pellet was re-suspended NZCYM broth (NZCYM broth: 10 g casein hydrolysate, 5 g yeast extract, 5 g NaCl, 1 g casamino acid and 2 g $MgSO_4.7H_2O$ in 1 liter of final volume in distilled/deionized water) containing 50 μg/ml spectinomycin to a final $A_{600}$ of 2.0. Cells were used within 1 h. To release the pExCell, 100 μl of the prepared NP66 cells were placed in a 15 ml sterile glass tube and incubated at 39° C. for 20 min to allow for expression of the H is proteins required for site-specific recombination between attL and attR sites. 100 μl of the phage SM solution was added from to the cells and incubated at 39° C. for an additional 20 min. To this NP66/phage mixture, 200 μl of 1 M sodium citrate was added to terminate the infection of NP66 with λ ExCell and 5 ml of pre-warmed (32° C.) 2×YT broth containing 50 μg/ml spectinomycin was added. The culture was incubated at 32° C. with moderate shaking for 1.5 h to yield 'released culture'. To prepare overnight cultures for subsequent isolation of pExCell DNA, 50 μl of the released culture was incubated at 37° C. in 5 ml of LB medium (LB medium: 10 g trypton, 5 g yeast extract, 10 g sodium chloride in 1 liter of final volume in distilled/deionized water) containing 100 μg/ml ampicillin.

EXAMPLE-6

Analysis and Sequencing of Cloned cDNA

The cultures were streaked and the colonies were randomly picked up using a pipette tip. The colony was suspended in 50 μl of lysis buffer (colony lysis buffer: TE (Tris-Cl10 mM, 1 mM EDTA, pH 8.0) with 0.1% tween 20), boiled for 10 min in a water bath followed by snap cooling on ice. Plasmid released in the colony lysate was amplified using 0.2 μM of each 'forward' (5'-GTTGTAAAACGACGGCCAGT-3') (SEQ ID NO: 22) and 'reverse' (5'-CACAGGAAACAGC-TATGACC-3') (SEQ ID NO: 14) flanking primer, 20 μM of dNTPs and 1 Units of *Thermus aqueticus* (hereinafter referred to Taq) DNA polymerase (purchased from M/S. Qiagen, Germany) in 1×PCR buffer (20 mM Tris-Cl (pH, 8.4), 50 mM KCl, 1.5 mM $MgCl_2$). In the present invention, dNTPs refers to deoxy nucleoside triphosphate which comprises of deoxyadenosine triphosphate (hereinafter referred to dATP), deoxyguanosine triphosphate (hereinafter referred to dGTP), deoxycytidine triphosphate (hereinafter referred to dCTP) and deoxythymidine triphosphate (hereinafter referred to dTTP). Thermocycler program consisted of 30 cycles of 94° C. for 40 sec, 52° C. for 1 min and 72° C. for 2 min. This was followed by a 5 min extension at 72° C. Amplified products were run on 1.2% agarose gel in 1×TAE buffer (TAE buffer: 0.04 M Tris-acetate, 0.002 M EDTA, pH 8.5) containing ethidium bromide (final concentration of 0.5 μg/ml) and analyzed for correct size of insert by comparing with standard DNA molecular weight marker. Plasmids were isolated using QIAGEN plasmid mini kit (Cat#12125). These were quantified, checked on 1% agarose gel and sequencing was performed using the BigDye terminator (version 3.1) cycle sequencing mix (Applied Biosystems, USA) on automated DNA sequencer (ABI Prism 310, Genetic Analyzer, Applied Biosystems, USA). Protocols were followed essentially as described by respective manufacturers. Sequencing primers used were 'forward' 5'-GTTGTAAAACGACGGC-CAGT-3' (SEQ ID NO: 22) and 'reverse' 5'-CACAGGAAA-CAGCTATGACC-3' (SEQ ID NO: 14).

INFORMATION FOR SEQ ID NO: 4
(i) SEQUENCE CHARACTERISTICS:
(A) LENGTH: 365 base pairs
(B) TYPE: nucleic acid
(C) STRANDEDNESS: double
(D) TOPOLOGY: circular
(ii) MOLECULE TYPE: cDNA
(iii) SEQUENCE DESCRIPTION:

SEQ ID NO: 4
5'CAAGAGGGAGATGGCCCAACTACTGTGACCGGAAACATTTCTGGCCTC

AAGCCTGGGCTTCATGGTTTCCATGTTCATGCTCTTGGGGACACAACCAA

TGGTTGCATGTCAACTGGACCACATTTCAATCCTGCTGGCAAAGAGCATG

GGTCTCCTGAAGATGAGACTCGTCATGCTGGTGATCTTGGAAATATCACT

GTTGGGGATGACGGAACTGCTTGCTTCACAATTGTTGACAAACAGATTCC

TCTCACTGGACCACACTCTATCATTGGTAGGGCTGTTGTTGTCCATGCAG

ATCCTGATGACCTTGGCAAGGGTGGACATGAGCTTAGCAAATCCACTGGA

AATGCTGGTGGCAGGAT 3'

EXAMPLE-7

Sequence mentioned in example 6 was searched for homology in the gene databases available at URL www.ncbi.nlm-.nih.gov. using Basic Local Alignment Search Tool (hereinafter called as BLAST). It was clear from the results that the sequence had a homology between 80-90% with the SOD sequences submitted in the databases.

EXAMPLE-8

Cloning of Full Length Gene Using Rapid Amplification of cDNA Ends (Hereinafter Referred to Race)

Rapid amplification of cDNA ends (RACE) was used to isolate full length SOD gene from *Potentilla atrosanguinea*. RACE amplifies DNA sequences from a messenger RNA template between a defined internal site and unknown sequences of either the 3' or 5' end (Frohman, M. A., Dush. M. K. and Martin, G. R. (1988) Proc. Natl. Acad. Sci. USA 85: 8998-9002; U.S. Pat. Nos. 5,962,271 and 5962272). A set of gene specific primers were used to generate 5' and 3' ends of the gene separately. The partial cDNA sequence (SEQ ID No; 1) was used to design two sets of primers. Primers were designed such that the amplified 5' and 3' ends overlap each other over a small stretch of nucleotides. For 5' RACE, a gene specific primer (hereinafter referred to GSP1), 5'-CCAGTG-GATTTGCTAAGCTCATGTCCA-3' (SEQ ID NO: 7) for primary PCR and one nested gene specific primer (hereinafter referred to NES1), 5'-GTCATCAGGGTCTGCATGGA-CAACAAC-3' (SEQ ID NO: 8) for secondary PCR (RACE). It has been used 1 μl of 10 μM nested primers stock for secondary PCR. For 3' RACE a gene specific primer (hereinafter referred to GSP2), 5'-ATGGTTGCATGTCAACTG-GACCACATT-3' (SEQ ID NO: 9) for primary PCR and one nested primer (hereinafter referred to NES2), 5'-TTGCAT-GTCAACTGGACCACATTTCAA-3' (SEQ ID NO: 10) were designed. Primers were designed such that the amplified 5' and 3' ends overlap each other over a small stretch of nucleotides.

The cDNA for 5'-RACE was synthesized using a modified lock-docking oligo(dT) primer and SMART II A oligo (dT) primer. The modified oligo (dT) primer, termed the 5'-RACE CDS Primer (5'-CDS) has two degenerate nucleotide positions at the 3' end.

1 μg of total RNA was reverse transcribed in separate reactions to yield 5' and 3' RACE ready cDNA using an enzyme known as reverse transcriptase. For 5' cDNA synthesis, the reaction was carried out using 1 μM of 5'-CDS primer in a reaction mixture containing RNA and 1 μM SMART II oligo (dT) primer. The 3'-RACE cDNA is synthesized using a traditional reverse transcription procedure, but with a special oligo (dT) primer. This 3'-RACE CDS Primer A (3'-CDS) primer includes the lock-docking nucleotide positions as in the 5'-CDS and also has a portion of the smart sequence at its 5' end. Sterile $H_2O$ was added to a final volume of 5 μl for each reaction, mixed and centrifuged. The reaction mix was incubated at 70° C. for 2 min and cooled on ice for 2 min. First-strand buffer (50 mM Tris-Cl (pH, 8.3), 75 mM KCl and 6 mM $MgCl_2$), 1 mM dNTPs, 2 mM DTT and reverse transcriptase were added to each reaction and incubated at 42° C. for 1.5 hr in an air incubator. Diluted the first-strand reaction product with 100 μl of Tricine-EDTA buffer (10 mM Tricine-KOH (pH 8.5), 1.0 mM EDTA) and heated tubes at 72° C. for 7 min. (Reverse transcription system was a component of SMART RACE cDNA amplification kit from BD Biosciences, USA).

Sequences of Primers used for RACE were as Follows (Purchased from BD Biosciences, USA as a Part of RACE Kit).

| Primer | Primer Sequence | |
|---|---|---|
| SMART II A Oligonucleotide | 5'-AAGCAGTGGTATCAACGCAGAGTACGCGGG-3' | (SEQ ID NO: 11) |
| 3'-RACE CDS Primer A (3'-CDS) | 5'-AAGCAGTGGTATCAACGCAGAGTAC(T)$_{30}$N$_{-1}$N-3' | (SEQ ID NO: 73) |
| 5'-RACE CDS Primer (5'-CDS) | 5'-(T)$_{25}$N$_{-1}$N-3' | (SEQ ID NO: 15) |
| 10X Universel Primer Mix A (UPM) | Long: 5'-TAATACGACTCACTATAGGGCAAGCAGTGGTATCAACGCAGAGT-3' | (SEQ ID NO: 16) |
| | Short: 5'-CTAATACGACTCACTATAGGGC-3' | (SEQ ID NO: 17) |
| Nested Universal Primer A (NUP) | 5'-AAGCAGTGGTATCAACGCAGAGT-3' | (SEQ ID NO: 23) |

5' and 3' RACE cDNA were amplified using 0.2 µM GSP1, GSP2 primer and 1× universal primer (UPM), 0.2 mM dNTP and 1×BD polymerase mix. Thermocycler program consisted of 30 cycles of 94° C. for 30 sec, 68° C. for 30 sec and 72° C. for 3 min. The reaction was up-scaled to 50 µl and after the completion of PCR, 45 µl of PCR sample was run on 1.2% agarose gel in TAE buffer containing ethidium bromide (final concentration of 0.5 µg/ml) Rest of the amplified product was stored at −20° C. for secondary PCR if needed. Amplicons were cut from the gel and DNA was eluted from the gel using QIAEX II gel extraction kit from M/S Qiagen, Germany following the manufacturer's instructions. The purified DNA was cloned in pGEM-T easy vector (Promega, USA), plasmids were isolated using the Qiagen plasmid mini-isolation kit, and sequencing was performed using the BigDye terminator (version 3.1) cycle sequencing mix (Applied Biosystems, USA) on an automated DNA sequencer (ABI Prism 310, Genetic Analyzer, Applied Biosystems). Protocols were followed essentially as described by respective manufacturers. The RACE products were analyzed by BLAST.

(3) INFORMATION FOR SEQ ID NO:2
 (i) SEQUENCE CHARACTERISTICS:
  (A) LENGTH: 856 base pairs
  (B) TYPE: nucleic acid
  (C) STRANDEDNESS: double
  (D) TOPOLOGY: circular
 (ii) MOLECULE TYPE: cDNA
 (iii) SEQUENCE DESCRIPTION:

SEQ ID NO: 2
5'ACGGGGGGGGACTGAAATAAATAGAGAGGGTCATAGTCACATTTGCA
TTTAGGTATCTGATTCCATTCACAAACCTCCAACTCCCACCTCTCTCT
ATTTCTCTTCATCTTCATCATCTTAGGGTGCACTGAGATCACTTTGAAAC
ATGGCAAAGGGCGTTGCTGTACTTAGCTCCAGTGAGGGTGTTGCTGGAAC
TATCCTCTTTACCCAAGAGGGAGATGGCCCAACTACTGTGACCGGAAACA
TTTCTGGCCTCAAGCCTGGGCTTCATGGTTTCCATGTTCATGCTCTTGGG
GACACAACCAATGGTTGCATGTCAACTGGACCACATTTCAATCCTGCTGG
CAAAGAGCATGGGTCTCCTGAAGATGAGACTCGTCATGCTGGTGATCTTG
GAAATATCACTGTTGGGGATGACGGAACTGCTTGCTTCACAATTGTTGAC

-continued

AAACAGATTCCTCTCACTGGACCACACTCTATCATTGGTAGGGCTGTTGT
TGTCCATGCAGATCCTGATGACCTTGGCAAGGGTGGACATGAGCTTAGCA
AATCCACTGGAAATGCTGGTGGCAGGATAGCTTGTGGTATTATTGGCCTT
CAAGGATGAACTGGACCAGGGAGCGAAACACAGGCATCTTGTTGAATTAA
AACTTGAGATATTAGCGAACTCTTCGGAATTGAGTATTGAAACAAGGAAT
ACATTTGTCATTACCAATACGTTTGGCTTAGACCTGTATTCTGTATCTCA
ATAGTTTTCTGTGTGGTTGTTTGACAGTTATTTGTGCTCAGGCTATTTCA
AAGGGATAAACACAGTAACTTTCTTGCTTTGACAAAAAAAAAAAAAAAA
AAAAAAAA 3'

EXAMPLE-9

Amplification of Coding Sequence (Hereinafter Known as CDS) of SOD and Cloning into an Expression Vector CDS of SOD was amplified by PCR using the forward primer 5'-ATGGCAAAGGGCGTTGCTGTACTT-3' (SEQ ID NO: 5) and reverse primer 5'-TCATCCTTGAAGGC-CAATAATACCA-3' (SEQ ID NO: 6) designed from start codon and stop codon. The amplified product was cloned into pQE 30 expression vector and transformed into competent E. coli cells. The plasmid was isolated using the standard plasmid isolation protocol (Sambrook, J., Fritsch, E. F. and Maniatis, T. 1989. Molecular Cloning: A Laboratory Manual, Cold Spring Harbor Laboratory Press, Plainview, N.Y.) and sequencing was performed using the BigDye terminator (version 3.1) cycle sequencing mix (Applied Biosystems, USA) on an automated DNA sequencer (ABI Prism 310, Genetic Analyzer, Applied Biosystems) to confirm cloning of insert. Protocols were followed essentially as described by the manufacturer.

(4) INFORMATION FOR SEQ ID NO:3
 (i) SEQUENCE CHARACTERISTICS:
  (A) LENGTH: 459 base pairs
  (B) TYPE: nucleic acid
  (C) STRANDEDNESS: double
  (D) TOPOLOGY: circular (ii) MOLECULE TYPE: cDNA
(iii) SEQUENCE DESCRIPTION:

SEQ ID NO: 3
5'ATGGCAAAGGGCGTTGCTGTACTTAGCTCCAGTGAGGGTGTTGCTGGA

ACTATCCTCTTTACCCAAGAGGGAGATGGCCCAACTACTGTGACCGGAAA

CATTTCTGGCCTCAAGCCTGGGCTTCATGGTTTCCATGTTCATGCTCTTG

GGGACACAACCAATGGTTGCATGTCAACTGGACCACATTTCAATCCTGCT

GGCAAAGAGCATGGGTCTCCTGAAGATGAGACTCGTCATGCTGGTGATCT

TGGAAATATCACTGTTGGGGATGACGGAACTGCTTGCTTCACAATTGTTG

ACAAACAGATTCCTCTCACTGGACCACACTCTATCATTGGTAGGGCTGTT

GTTGTCCATGCAGATCCTGATGACCTTGGCAAGGGTGGACATGAGCTTAG

CAAATCCACTGGAAATGCTGGTGGCAGGATAGCTTGTGGTATTATTGGCC

TTCAAGGATGA 3'

(5) INFORMATION FOR Pro SEQ ID NO:1
(i) SEQUENCE CHARACTERISTICS:
(A) LENGTH: 152 amino acids
(B) TYPE: amino acid
(ii) MOLECULE TYPE: polypeptide
(iii) SEQUENCE DESCRIPTION:

SEQ ID NO: 1
MAKGVAVLSSSEGVAGTILFTQEGDGPTTVTGNISGLKPGLHGFHVHALG

DTTNGCMSTGPHFNPAGKEHGSPEDETRHAGDLGNITVGDDGTACFTIVD

KQIPLTGPHSIIGRAVVVHADPDDLGKGGHELSKSTGNAGGRIACGIIGL

QG

EXAMPLE-10

Induction and Purification of Expressed Protein

E. coli containing SOD gene from Potentilla was grown at 37° C. in 100 ml of LB medium with 100 μg ml$^{-1}$ and 25 μg ml$^{-1}$ kanamycin. When that culture had grown to an absorbance of 0.6 at 600 nm, IPTG was added to a final concentration of 1 mM. CuSO$_4$ and ZnSO$_4$ were added to a final concentration of 100 ppm and 2 ppm, respectively. After inducing the expression of the SOD protein for 5 h at 37° C., cells were harvested, washed and resuspended in 4 ml of lysis buffer (50 mM NaH$_2$PO$_4$ buffer, pH 8.0, containing 300 mM NaCl and 10 mM imidazole). The cell suspension was sonicated, and the lysate was cleared by centrifugation at 12000 g and 4° C. for 20 min. The supernatant was then poured into the column loaded with nickel-nitrilotriacitic acid (Ni-NTA) agarose, washed with wash buffer (50 mM NaH$_2$PO$_4$ buffer, pH 8.0, containing 300 mM NaCl and 20 mM imidazole), and SOD protein was eluted with elution buffer (50 mM NaH$_2$PO$_4$ buffer, pH 8.0, containing 300 mM NaCl and 250 mM imidazole). The purified SOD was evaluated by 10% SDS-PAGE using silver staining to visualize the protein (FIG. 4A).

The protein estimation was performed, before and after autoclaving purified SOD that shows ±25% loss of protein. Since 50 μl of protein sample was used for assaying SOD activity, the loss in protein was calculated while calculating the enzyme activity. Reaction medium contained 0.05 M potassium phosphate buffer (pH, 7.0), 5.7×10$^{-5}$ M nitroblue tetrazolium (hereinafter referred to NBT), 9.9×10$^{-3}$ M methionine, 1.17×10$^{-6}$ M riboflavin and 0.025% Triton X-100 in a total volume of 3.0 ml. Reaction (performed in a 30 ml glass vial) was initiated by illuminating the reaction with light intensity of 1000μ Einstein/m$^2$/ second using a fiber optic light source (Nikon). The reaction was terminated after 2 min and the absorbance was read at 560 nm.

A control reaction was always performed wherein all the steps and components were exactly the same as described above except that purified enzyme was replaced with equal volume of homogenizing buffer. Activity of SOD is expressed as percent inhibition in color development as compared to the control reaction (higher the inhibition, higher the SOD activity). Activity data was shown in FIG. 1.

EXAMPLE-11

SOD Activity at Different Temperatures in Purified SOD

The purified SOD enzyme was assayed at temperatures ranging between –10 to 80° C. in the buffer composition as described in Example 10 except that 50% glycerol was added in the reaction mixture to avoid freezing at low temperature. A glass beaker of 100 ml capacity was filled with either alcohol (for working at temperatures of –10, –5, 0° C.) or distilled water (for working at rest of the temperatures) was used to maintain the temperature of the reaction medium while assaying SOD. Reaction medium along with the enzyme was pre-equilibrated at desired temperature to avoid time lag in attaining the required temperature. As can be seen from FIG. 1 that the enzyme showed highest activity (87.5% inhibition) at 0° C. The enzyme was functional even up to –10° C. (82% inhibition). The enzyme is expected at temperature lower than –10° C.

Control reactions, as mentioned in Example 10, were always performed at all the temperatures.

EXAMPLE-12

Localization of SOD by Activity Staining of Native Gel

The purified SOD was localized on 10% polyacrylamide gel by activity staining as described by Beauchamp and Fridovich (Anal. Biochem. 1971; 44: 246-287). After electrophoresis, the gel was rinsed with distilled water followed by 30 min incubation in 50 ml phosphate buffer (50 mM; pH 7.0) containing 2.5 mM NBT in dark at room temperature. Gel was then immersed in 1.17×10$^{-6}$ M riboflavin for 20 min, followed by exposure to light source (Nikon). Light exposure led to photogeneration of O$_2^-$, which converts NBT into insoluble purple colored formazan. The purple color was developed throughout the gel except for the location where SOD was localized as shown in FIG. 4B.

Advantages:
The main advantages of the present invention are:
1. SOD gene has been cloned from Potentilla that is autoclavable and functions at sub-zero temperature.
2. SOD gene that is isolated from Potentilla has been made to express in E. coli.
3. SOD gene from Potentilla that is made to express in E. coli leading to synthesis of SOD protein that is autoclavable.
4. SOD gene from Potentilla that is made to express in E. coli leading to synthesis of SOD protein that is autoclavable, also functions at sub-zero temperature.

SEQUENCE LISTING

<160> NUMBER OF SEQ ID NOS: 73

<210> SEQ ID NO 1
<211> LENGTH: 152
<212> TYPE: PRT
<213> ORGANISM: Potentilla atrosanguinea

<400> SEQUENCE: 1

```
Met Ala Lys Gly Val Ala Val Leu Ser Ser Glu Gly Val Ala Gly
 1               5                  10                  15

Thr Ile Leu Phe Thr Gln Glu Gly Asp Gly Pro Thr Thr Val Thr Gly
            20                  25                  30

Asn Ile Ser Gly Leu Lys Pro Gly Leu His Gly Phe His Val His Ala
        35                  40                  45

Leu Gly Asp Thr Thr Asn Gly Cys Met Ser Thr Gly Pro His Phe Asn
    50                  55                  60

Pro Ala Gly Lys Glu His Gly Ser Pro Glu Asp Glu Thr Arg His Ala
65                  70                  75                  80

Gly Asp Leu Gly Asn Ile Thr Val Gly Asp Asp Gly Thr Ala Cys Phe
                85                  90                  95

Thr Ile Val Asp Lys Gln Ile Pro Leu Thr Gly Pro His Ser Ile Ile
            100                 105                 110

Gly Arg Ala Val Val Val His Ala Asp Pro Asp Asp Leu Gly Lys Gly
        115                 120                 125

Gly His Glu Leu Ser Lys Ser Thr Gly Asn Ala Gly Gly Arg Ile Ala
    130                 135                 140

Cys Gly Ile Ile Gly Leu Gln Gly
145                 150
```

<210> SEQ ID NO 2
<211> LENGTH: 856
<212> TYPE: DNA
<213> ORGANISM: Potentilla atrosanguinea

<400> SEQUENCE: 2

```
acggggggg gactgaaata aatagagagg gtcatagtca catttgcatt taggtatctg      60
attccattca caaacctcca actcccacct ctctctctat ttctcttcat cttcatcatc    120
ttagggtgca ctgagatcac tttgaaacat ggcaaagggc gttgctgtac ttagctccag    180
tgagggtgtt gctggaacta tcctctttac ccaagaggga gatggcccaa ctactgtgac    240
cggaaacatt tctggcctca agcctgggct tcatggtttc catgttcatg ctcttgggga    300
cacaaccaat ggttgcatgt caactggacc acatttcaat cctgctggca aagagcatgg    360
gtctcctgaa gatgagactc gtcatgctgg tgatcttgga aatatcactg ttggggatga    420
cggaactgct gcttcacaa ttgttgacaa acagattcct ctcactggac cacactctat    480
cattggtagg gctgttgttg tccatgcaga tcctgatgac cttggcaagg gtggacatga    540
gcttagcaaa tccactggaa atgctggtgg caggatagct gtgggtatta ttggccttca    600
aggatgaact ggaccaggga gcgaaacaca ggcatcttgt tgaattaaaa cttgagatat    660
tagcgaactc ttcggaattg agtattgaaa caaggaatac atttgtcatt accaatacgt    720
ttggcttaga cctgtattct gtatctcaat agttttctgt gtggttgttt gacagttatt    780
tgtgctcagg ctatttcaaa gggataaaca cagtaacttt cttgctttga caaaaaaaa    840 aaaaaaaaa aaaaaa                                                     856
```

<210> SEQ ID NO 3
<211> LENGTH: 459
<212> TYPE: DNA
<213> ORGANISM: Potentilla atrosanguinea

<400> SEQUENCE: 3

```
atggcaaagg gcgttgctgt acttagctcc agtgagggtg ttgctggaac tatcctcttt      60
acccaagagg gagatggccc aactactgtg accggaaaca tttctggcct caagcctggg     120
cttcatggtt tccatgttca tgctcttggg gacacaacca atggttgcat gtcaactgga     180
ccacatttca atcctgctgg caaagagcat gggtctcctg aagatgagac tcgtcatgct     240
ggtgatcttg gaaatatcac tgttggggat gacggaactg cttgcttcac aattgttgac     300
aaacagattc ctctcactgg accacactct atcattggta gggctgttgt tgtccatgca     360
gatcctgatg accttggcaa gggtggacat gagcttagca aatccactgg aaatgctggt     420
ggcaggatag cttgtggtat tattggcctt caaggatga                            459
```

<210> SEQ ID NO 4
<211> LENGTH: 365
<212> TYPE: DNA
<213> ORGANISM: Potentilla atrosanguinea

<400> SEQUENCE: 4

```
caagagggag atggcccaac tactgtgacc ggaaacattt ctggcctcaa gcctgggctt      60
catggtttcc atgttcatgc tcttggggac acaaccaatg gttgcatgtc aactggacca     120
catttcaatc ctgctggcaa agagcatggg tctcctgaag atgagactcg tcatgctggt     180
gatcttggaa atatcactgt tggggatgac ggaactgctt gcttcacaat tgttgacaaa     240
cagattcctc tcactggacc acactctatc attggtaggg ctgttgttgt ccatgcagat     300
cctgatgacc ttggcaaggg tggacatgag cttagcaaat ccactggaaa tgctggtggc     360
aggat                                                                 365
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
atggcaaagg gcgttgctgt actt                                             24
```

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
tcatccttga aggccaataa tacca                                            25
```

<210> SEQ ID NO 7
<211> LENGTH: 27
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 7
ccagtggatt tgctaagctc atgtcca                                           27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtcatcaggg tctgcatgga caacaac                                           27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atggttgcat gtcaactgga ccacatt                                           27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgcatgtca actggaccac atttcaa                                           27

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aagcagtggt atcaacgcag agtacgcggg                                        30

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(28)
<223> OTHER INFORMATION: a, c, g, t, unknown or other

<400> SEQUENCE: 12
aagcagtggt atcaacgcag agtactnn                                          28

<210> SEQ ID NO 13
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gttgtaaaac gacgtgccag t                                              21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cacaggaaac agctatgacc                                                20

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: a, c, g, t, unknown or other

<400> SEQUENCE: 15
tttttttttt tttttttttt tttttnn                                        27

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
taatacgact cactataggg caagcagtgg tatcaacgca gagt                      44

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctaatacgac tcactatagg gc                                              22

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aactggaaga attcgcggcc gcaggaattt tttttttttt ttttt                     45
```

```
<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tttttttttt tttttttt                                                        18

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aattcggcac gagg                                                            14

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gccgtgctcc                                                                 10

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gttgtaaaac gacggccagt                                                      20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aagcagtggt atcaacgcag agt                                                  23

<210> SEQ ID NO 24
<211> LENGTH: 459
<212> TYPE: DNA
<213> ORGANISM: Malus sp.

<400> SEQUENCE: 24
atggtgaagg gtgttgctgt tctcggctcc agtgagggcg ttaaaggaac catcagcttt          60
gtccaggagg gagatgggcc aactactgtg actggaagtg tctctggcct caagcctgga         120
cttcatggtt tccatgtcca tgctcttgga gacacaacaa acggttgcat gtcaactggg         180
```

```
ccacacttca atcctgctgg aaaagagcat ggtgccoctg aagatgagct tcgccatgct    240
ggcgatcttg gaaacatcac tgctggggac gatggaactg caaccttcac gattgttgac    300
aagcagattc ctctcgctgg accacactct atcattggta gggcggttgt tgtccacgca    360
gaccctgatg accttggcaa gggtggacat gagcttagca aatccacagg aaatgctggt    420
ggcagggtgg cttgcggtat tattggtctg caaggatga                           459
```

<210> SEQ ID NO 25
<211> LENGTH: 459
<212> TYPE: DNA
<213> ORGANISM: Populus sp.

<400> SEQUENCE: 25

```
atggtgaagg ctgtagctgt tcttaatagc agtgaaggtg tgagtggcac catcttcttt    60
acccaagaag gagatggccc aactactgta attggaaacc tttctggtct taagccaggc   120
cttcatggct ccacgtcca  tgcccttgga gacaccacaa atggctgcat gtcaactggg   180
ccgcatttta atcctgtagg caaggagcat ggtgcccctg aggatgagaa tcgtcatgct   240
ggtgatctgg aaatgtcac  tgttggtgat gatggcactg ctgctttcac aatcattgac   300
aaacagattc ctcttactgg accacattcc attattggtt gggctgttgt tgttcatgga   360
gatcctgatg atcttggcaa gggaggacat gaactcagca aaaccactgg taatgctggc   420
ggcagagtag catgcggtat tattggtctg caaggttga                          459
```

<210> SEQ ID NO 26
<211> LENGTH: 459
<212> TYPE: DNA
<213> ORGANISM: Zea sp.

<400> SEQUENCE: 26

```
atggtgaagg ctgtggcagt tcttagtaac agtaacgaag tctcgggtac tattaacttc    60
agtcaggagg gaaatggtcc aaccactgta actggaactc ttgctggtct taagcctggc   120
ctccacggct tccatatcca tgccttggga gacaccacaa acggttgcat ttcaactgga   180
ccacatttca atcctaatgg gaaggaacat ggtgcccctg aggatgagac tagacatgct   240
ggtgatcttg gaaatatcaa tgttggtgat gatggaactg taagcttcac cattactgac   300
aaccatatcc ctctcactgg aacaaactcc atcataggaa gggctgttgt tgtccatgcc   360
gatcctgatg atcttgggaa aggtggtcac gagcttagca aaactactgg aaatgctggt   420
ggcagagtag cttgtggtat tattgggttg caaggatag                          459
```

<210> SEQ ID NO 27
<211> LENGTH: 459
<212> TYPE: DNA
<213> ORGANISM: Arabidopsis sp.

<400> SEQUENCE: 27

```
atggcgaaag gagttgcagt tttgaacagc agtgagggtg ttacggggac tatctttttc    60
acccaggaag gcgatggtgt gaccactgtg agtggaacag tttctggcct taagcctggt   120
cttcatggtt ccatgtcca  tgctcttggt gacaccacta acggttgcat gtctactggt   180
ccacatttca accccgatgg taaaacacac ggtgcccctg aggatgctaa tcgacatgct   240
ggtgatctag gaaacatcac tgtggagat  gatggaactg ccaccttcac aatcactgat   300
tgccagattc ctcttactgg accaaactct attgttggta gggctgttgt tgtccatgca   360
gaccctgatg acctcggaaa gggaggccat gaactcagcc tggctactgg aaacgcaggc   420
```

```
ggccgtgttg cttgcggcat cattggtctc cagggctaa                    459
```

<210> SEQ ID NO 28
<211> LENGTH: 459
<212> TYPE: DNA
<213> ORGANISM: Oryza sp.

<400> SEQUENCE: 28

```
atggtgaagg ctgttgctgt gcttgctagc agtgagggtg tcaagggcac catctttttc    60
tcccaagagg gagatggtcc gacctctgtg acgggaagtg tctctgggct caagccaggg   120
ctccatggat tccatgtgca cgcgctcggt gacaccacta atggctgcat gtcaactgga   180
ccacacttca atcctactgg gaaggaacat ggggcaccac aagatgagaa ccgccatgcc   240
ggtgatcttg gaaatataac agctggagca gatggtgttg ctaatgtcaa tgtctctgac   300
agccagatcc cccttactgg agcacactcc atcattggcc gagctgttgt tgtccatgct   360
gatcctgatg atcttggcaa gggtggacat gagcttagca agaccactgg aaatgctggg   420
ggccgagttg cttgcggaat catcggactc cagggttag                          459
```

<210> SEQ ID NO 29
<211> LENGTH: 152
<212> TYPE: PRT
<213> ORGANISM: Malus sp.

<400> SEQUENCE: 29

```
Met Val Lys Gly Val Ala Val Leu Gly Ser Ser Glu Gly Val Lys Gly
  1               5                  10                  15

Thr Ile Ser Phe Val Gln Glu Gly Asp Gly Pro Thr Thr Val Thr Gly
             20                  25                  30

Ser Val Ser Gly Leu Lys Pro Gly Leu His Gly Phe His Val His Ala
         35                  40                  45

Leu Gly Asp Thr Thr Asn Gly Cys Met Ser Thr Gly Pro His Phe Asn
     50                  55                  60

Pro Ala Gly Lys Glu His Gly Ala Pro Glu Asp Glu Leu Arg His Ala
 65                  70                  75                  80

Gly Asp Leu Gly Asn Ile Thr Ala Gly Asp Gly Thr Ala Thr Phe
             85                  90                  95

Thr Ile Val Asp Lys Gln Ile Pro Leu Ala Gly Pro His Ser Ile Ile
            100                 105                 110

Gly Arg Ala Val Val His Ala Asp Pro Asp Leu Gly Lys Gly
        115                 120                 125

Gly His Glu Leu Ser Lys Ser Thr Gly Asn Ala Gly Arg Val Ala
    130                 135                 140

Cys Gly Ile Ile Gly Leu Gln Gly
145                 150
```

<210> SEQ ID NO 30
<211> LENGTH: 152
<212> TYPE: PRT
<213> ORGANISM: Arabidopsis sp.

<400> SEQUENCE: 30

```
Met Ala Lys Gly Val Ala Val Leu Asn Ser Ser Glu Gly Val Thr Gly
  1               5                  10                  15

Thr Ile Phe Phe Thr Gln Glu Gly Asp Gly Val Thr Thr Val Ser Gly
             20                  25                  30
```

```
Thr Val Ser Gly Leu Lys Pro Gly Leu His Gly Phe His Val His Ala
        35                  40                  45

Leu Gly Asp Thr Thr Asn Gly Cys Met Ser Thr Gly Pro His Phe Asn
    50                  55                  60

Pro Asp Gly Lys Thr His Gly Ala Pro Glu Asp Ala Asn Arg His Ala
65                  70                  75                  80

Gly Asp Leu Gly Asn Ile Thr Val Gly Asp Gly Thr Ala Thr Phe
                85                  90                  95

Thr Ile Thr Asp Cys Gln Ile Pro Leu Thr Gly Pro Asn Ser Ile Val
            100                 105                 110

Gly Arg Ala Val Val His Ala Asp Pro Asp Leu Gly Lys Gly
        115                 120                 125

Gly His Glu Leu Ser Leu Ala Thr Gly Asn Ala Gly Arg Val Ala
    130                 135                 140

Cys Gly Ile Ile Gly Leu Gln Gly
145                 150

<210> SEQ ID NO 31
<211> LENGTH: 152
<212> TYPE: PRT
<213> ORGANISM: Populus sp.

<400> SEQUENCE: 31

Met Val Lys Ala Val Ala Val Leu Asn Ser Ser Glu Gly Val Ser Gly
1               5                   10                  15

Thr Ile Phe Phe Thr Gln Glu Gly Asp Gly Pro Thr Thr Val Thr Gly
            20                  25                  30

Asn Leu Ser Gly Leu Lys Pro Gly Leu His Gly Phe His Val His Ala
        35                  40                  45

Leu Gly Asp Thr Thr Asn Gly Cys Met Ser Thr Gly Pro His Phe Asn
    50                  55                  60

Pro Val Gly Lys Glu His Gly Ala Pro Glu Asp Glu Asn Arg His Ala
65                  70                  75                  80

Gly Asp Leu Gly Asn Val Thr Val Gly Asp Asp Gly Thr Ala Ala Phe
                85                  90                  95

Thr Ile Ile Asp Phe Gln Ile Pro Leu Thr Gly Pro His Ser Ile Ile
            100                 105                 110

Gly Arg Ala Val Val His Gly Asp Pro Asp Asp Leu Gly Lys Gly
        115                 120                 125

Gly His Glu Leu Ser Lys Thr Thr Gly Asn Ala Gly Gly Arg Val Ala
    130                 135                 140

Cys Gly Ile Ile Gly Leu Gln Gly
145                 150

<210> SEQ ID NO 32
<211> LENGTH: 152
<212> TYPE: PRT
<213> ORGANISM: Oryza sp.

<400> SEQUENCE: 32

Met Val Lys Ala Val Val Leu Gly Ser Ser Glu Ile Val Lys Gly
1               5                   10                  15

Thr Ile His Phe Val Gln Glu Gly Asp Gly Pro Thr Thr Val Thr Gly
            20                  25                  30

Ser Val Ser Gly Leu Lys Pro Gly Leu His Gly Phe His Ile His Ala
        35                  40                  45
```

```
Leu Gly Asp Thr Thr Asn Gly Cys Met Ser Thr Gly Pro His Tyr Asn
 50                  55                  60

Pro Ala Gly Lys Glu His Gly Ala Pro Glu Asp Glu Thr Arg His Ala
 65                  70                  75                  80

Gly Asp Leu Gly Asn Val Thr Ala Gly Glu Asp Gly Val Ala Asn Ile
                 85                  90                  95

His Val Val Asp Ser Gln Ile Pro Leu Thr Gly Pro Asn Ser Ile Ile
            100                 105                 110

Gly Arg Ala Val Val His Ala Asp Pro Asp Leu Gly Lys Gly
        115                 120                 125

Gly His Glu Leu Ser Lys Thr Thr Gly Asn Ala Gly Arg Val Ala
    130                 135                 140

Cys Gly Ile Ile Gly Leu Gln Gly
145                 150

<210> SEQ ID NO 33
<211> LENGTH: 152
<212> TYPE: PRT
<213> ORGANISM: Zea sp.

<400> SEQUENCE: 33

Met Val Lys Ala Val Ala Val Leu Gly Ser Glu Gly Val Lys Gly
  1               5                  10                  15

Thr Ile Phe Phe Thr Gln Glu Gly Asp Gly Pro Thr Thr Val Thr Gly
                 20                  25                  30

Ser Val Ser Gly Leu Lys Pro Gly Leu His Gly Phe His Val His Ala
             35                  40                  45

Leu Gly Asp Thr Thr Asn Gly Cys Met Ser Thr Gly Pro His Tyr Asn
 50                  55                  60

Pro Ala Ser Lys Glu His Gly Ala Pro Glu Asp Glu Asn Arg His Ala
 65                  70                  75                  80

Gly Asp Leu Gly Asn Val Thr Ala Gly Ala Asp Gly Val Ala Asn Ile
                 85                  90                  95

Asn Val Thr Asp Ser Gln Ile Pro Leu Thr Gly Pro Asn Ser Ile Ile
            100                 105                 110

Gly Arg Ala Val Val His Ala Asp Pro Asp Leu Gly Lys Gly
        115                 120                 125

Gly His Glu Leu Ser Lys Ser Thr Gly Asn Ala Gly Arg Val Ala
    130                 135                 140

Cys Gly Ile Ile Gly Leu Gln Gly
145                 150

<210> SEQ ID NO 34
<211> LENGTH: 152
<212> TYPE: PRT
<213> ORGANISM: Gossypium sp.

<400> SEQUENCE: 34

Met Val Lys Ala Val Ala Val Leu Gly Ser Asn Glu Gly Val Ser Gly
  1               5                  10                  15

Thr Val Phe Phe Ser Gln Glu Gly Asp Gly Pro Thr Thr Val Thr Gly
                 20                  25                  30

Asn Leu Ser Gly Leu Lys Pro Gly Leu His Gly Phe His Val His Ala
             35                  40                  45

Leu Gly Asp Thr Thr Asn Gly Cys Met Ser Thr Gly Pro His Phe Asn
 50                  55                  60
```

```
Pro Ala Gly Lys Glu His Gly Ala Pro Glu Asp Glu Asn Arg His Ala
 65                  70                  75                  80

Gly Asp Leu Gly Asn Val Thr Val Gly Asp Gly Cys Ala Ser Phe
                 85                  90                  95

Ser Ile Thr Asp Lys Gln Ile Pro Leu Thr Gly Pro Asn Ser Ile Ile
             100                 105                 110

Gly Arg Ala Val Val His Ala Asp Pro Asp Leu Gly Lys Gly
         115                 120                 125

Gly His Glu Leu Ser Lys Ser Thr Gly Asn Ala Gly Arg Val Ala
         130                 135                 140

Cys Gly Ile Ile Gly Leu Gln Gly
145                 150
```

<210> SEQ ID NO 35
<211> LENGTH: 152
<212> TYPE: PRT
<213> ORGANISM: Pisum sp.

<400> SEQUENCE: 35

```
Met Val Lys Ala Val Ala Val Leu Ser Asn Ser Asn Glu Val Ser Gly
  1               5                  10                  15

Thr Ile Asn Phe Ser Gln Glu Gly Asn Gly Pro Thr Thr Val Thr Gly
                 20                  25                  30

Thr Leu Ala Gly Leu Lys Pro Gly Leu His Gly Phe His Ile His Ala
             35                  40                  45

Leu Gly Asp Thr Thr Asn Gly Cys Ile Ser Thr Gly Pro His Phe Asn
 50                  55                  60

Pro Asn Gly Lys Glu His Gly Ala Pro Glu Asp Glu Thr Arg His Ala
 65                  70                  75                  80

Gly Asp Leu Gly Asn Ile Asn Val Gly Asp Asp Gly Thr Val Ser Phe
                 85                  90                  95

Thr Ile Thr Asp Asn His Ile Pro Leu Thr Gly Thr Asn Ser Ile Ile
             100                 105                 110

Gly Arg Ala Val Val His Ala Asp Pro Asp Asp Leu Gly Lys Gly
         115                 120                 125

Gly His Glu Leu Ser Lys Thr Thr Gly Asn Ala Gly Arg Val Ala
         130                 135                 140

Cys Gly Ile Ile Gly Leu Gln Gly
145                 150
```

<210> SEQ ID NO 36
<211> LENGTH: 152
<212> TYPE: PRT
<213> ORGANISM: Glycine max

<400> SEQUENCE: 36

```
Met Val Lys Ala Val Ala Val Leu Gly Ser Ser Glu Gly Val Thr Gly
  1               5                  10                  15

Thr Ile Phe Phe Thr Gln Glu Gly Asn Gly Pro Thr Thr Val Thr Gly
                 20                  25                  30

Ser Leu Ala Gly Leu Lys Pro Gly Leu His Gly Phe His Val His Ala
             35                  40                  45

Leu Gly Asp Thr Thr Asn Gly Cys Leu Ser Thr Gly Ala His Phe Asn
 50                  55                  60

Pro Asn Asn Asn Glu His Gly Ala Pro Glu Asp Glu Asn Arg His Ala
 65                  70                  75                  80
```

```
Gly Asp Leu Gly Asn Val Asn Val Gly Asp Asp Gly Thr Val Ser Phe
                85                  90                  95
Ser Ile Thr Asp Ser Gln Ile Pro Leu Thr Gly Pro Asn Ser Ile Ile
            100                 105                 110
Gly Arg Ala Val Val His Ala Asp Ser Asp Asp Leu Gly Lys Gly
        115                 120                 125
Gly His Glu Leu Ser Lys Thr Thr Gly Asn Ala Gly Arg Val Ala
    130                 135                 140
Cys Gly Ile Ile Gly Leu Gln Gly
145                 150

<210> SEQ ID NO 37
<211> LENGTH: 394
<212> TYPE: DNA
<213> ORGANISM: Ipomoea batatas

<400> SEQUENCE: 37
tcttcagcca agaaggagat ggtccaacca cagtcactgg aaacgtttcg ggcctcaaac      60
ctggtcttca tggcttccat gtccatgccc taggtgacac aacaaatgga tgcatgtcta     120
ctggaccaca tttcaatcct gctggaaagg agcatggagc tcctggagac gataaccgcc     180
atgccggtga tcttggaaac atcacggttg gagaagatgg tactgcttca ttcaccatca     240
ctgacaagca gattccgctt actggagcaa attctgttat tggaagagct gttgttgttc     300
atggtgatcc cgatgatctt ggtaaaggtg gccatgagct cagcaaaagc actggaaatg     360
ctggcgggag ggttgcctgc ggtatcattg gcct                                 394

<210> SEQ ID NO 38
<211> LENGTH: 394
<212> TYPE: DNA
<213> ORGANISM: Potentilla atrosanguinea

<400> SEQUENCE: 38
tctttaccca agagggagat ggcccaacta ctgtgaccgg aaacatttct ggcctcaagc      60
ctgggcttca tggtttccat gttcatgctc ttggggacac aaccaatggt tgcatgtcaa     120
ctggaccaca tttcaatcct gctggcaaag agcatgggtc tcctgaagat gagactcgtc     180
atgctggtga tcttggaaat atcactgttg ggatgacgg aactgcttgc ttcacaattg      240
ttgacaaaca gattcctctc actggaccac actctatcat tggtagggct gttgttgtcc     300
atgcagatcc tgatgacctt ggcaagggtg gacatgagct tagcaaatcc actggaaatg     360
ctggtggcag gatagcttgt ggtattattg gcct                                 394

<210> SEQ ID NO 39
<211> LENGTH: 459
<212> TYPE: DNA
<213> ORGANISM: Potentilla atrosanguinea

<400> SEQUENCE: 39
atggcaaagg gcgttgctgt acttagctcc agtgagggtg ttgctggaac tatcctcttt      60
acccaagagg gagatggccc aactactgtg accggaaaca tttctggcct caagcctggg     120
cttcatggtt tccatgttca tgctcttggg gacacaacca atggttgcat gtcaactgga     180
ccacatttca atcctgctgg caaagagcat gggtctcctg aagatgagac tcgtcatgct     240
ggtgatcttg gaaatatcac tgttggggat gacggaactg cttgcttcac aattgttgac     300
aaacagattc ctctcactgg accacactct atcattggta gggctgttgt tgtccatgca     360
```

-continued

```
gatcctgatg accttggcaa gggtggacat gagcttagca aatccactgg aaatgctggt    420
ggcaggatag cttgtggtat tattggcctt caaggatga                           459
```

<210> SEQ ID NO 40
<211> LENGTH: 459
<212> TYPE: DNA
<213> ORGANISM: Fagus sylvatica

<400> SEQUENCE: 40

```
atggccaagg gtgtggctgt tcttagctcg aatgagggtg tttgtggcac tatctacttt    60
gcccaagaag gagatggccc aactacagta actggaaata tttctggcct taaacctgga    120
ctccatggct tccacgtgca tgctcttggg gacacaacaa atggttgcat gtcaactgga    180
ccacatttca atcctgctgg caaagagcat ggtgctcctg aggatgcgaa tcgtcatgct    240
ggtgatctgg gaaatgtcaa tgttggtgat gatggcacag tcagtttcac aataattgac    300
aaacagattc cactttgtgg tccaaattcc attatcggaa gggctgttgt tgtccatgga    360
gatccagatg atcttggcaa gggggggacat gaacttagca agagcactgg aaatgctggt    420
ggccgtatag cttgtggtat cattggtctc caaggatga                           459
```

<210> SEQ ID NO 41
<211> LENGTH: 400
<212> TYPE: DNA
<213> ORGANISM: Potentilla atrosanguinea

<400> SEQUENCE: 41

```
tctttaccca agagggagat ggcccaacta ctgtgaccgg aaacatttct ggcctcaagc    60
ctgggcttca tggtttccat gttcatgctc ttggggacac aaccaatggt tgcatgtcaa    120
ctggaccaca tttcaatcct gctggcaaag agcatgggtc tcctgaagat gagactcgtc    180
atgctggtga tcttggaaat atcactgttg gggatgacgg aactgcttgc ttcacaattg    240
ttgacaaaca gattcctctc actggaccac actctatcat tggtagggct gttgttgtcc    300
atgcagatcc tgatgacctt ggcaagggtg gacatgagct tagcaaatcc actggaaatg    360
ctggtggcag gatagcttgt ggtattattg gccttcaagg                          400
```

<210> SEQ ID NO 42
<211> LENGTH: 400
<212> TYPE: DNA
<213> ORGANISM: Populus tremuloides

<400> SEQUENCE: 42

```
tctttaccca agaaggagat ggcccaacta ctgtaattgg aaacctttct ggtcttaagc    60
caggccttca tggcttccac gtccatgccc ttggagacac cacaaatggc tgcatgtcaa    120
ctgggccgca ttttaatcct gtaggcaagg agcatggtgc ccctgaggat gagaatcgtc    180
atgctggtga tctgggaaat gtcactgttg gtgatgatgg cactgctgct ttcacaatca    240
ttgacaaaca gattcctctt actggaccac attccattat tggttgggct gttgttgttc    300
atggagatcc tgatgatctt ggcaaggggag gacatgaact cagcaaaacc actggtaatg    360
ctggcggcag agtagcatgc ggtattattg gtctgcaagg                          400
```

<210> SEQ ID NO 43
<211> LENGTH: 416
<212> TYPE: DNA
<213> ORGANISM: Potentilla atrosanguinea

<400> SEQUENCE: 43

```
agtgagggtg ttgctggaac tatcctcttt acccaagagg gagatggccc aactactgtg    60
accggaaaca tttctggcct caagcctggg cttcatggtt tccatgttca tgctcttggg   120
gacacaacca atggttgcat gtcaactgga ccacatttca atcctgctgg caaagagcat   180
gggtctcctg aagatgagac tcgtcatgct ggtgatcttg aaatatcac tgttggggat    240 gacggaactg cttgcttcac aattgttgac aaacagattc ctctcactgg accacactct   300
atcattggta gggctgttgt tgtccatgca gatcctgatg accttggcaa gggtggacat   360
gagcttagca atccactgg aaatgctggt ggcaggatag cttgtggtat tattgg        416
```

<210> SEQ ID NO 44
<211> LENGTH: 416
<212> TYPE: DNA
<213> ORGANISM: Manihot esculenta

<400> SEQUENCE: 44

```
agtgagggtg ttgctgggac aatcttcttc acccaagaag gagatggtcc aaccaccgtc    60
actggaagtg tttctggcct taagccaggg cttcatggat tccatgttca tgcccttgga   120
gacacaacaa atggttgcat gtcaactggg ccacatttca accctggtgg caaagagcat   180
ggtgcccctg aggacgacat tcgtcatgct ggtgatctgg aaatgtcac tgctggtgat    240 gatggcactg ctagtttcac aatcgttgac aaggatattc ctctttctgg tccgcattcc   300
attgtaggaa gggcagtcgt tgttcatgca gatcctgatg atcttggaaa gggggacat    360 gaacttagca aaaccactgg aaatgctggt ggcagggtag catgtggtgt tattgg       416
```

<210> SEQ ID NO 45
<211> LENGTH: 331
<212> TYPE: DNA
<213> ORGANISM: Potentilla atrosanguinea

<400> SEQUENCE: 45

```
actatcctct ttacccaaga gggagatggc ccaactactg taccggaaaa catttctggc    60
ctcaagcctg gcttcatgg tttccatgtt catgctcttg ggacacaac caatggttgc    120 atgtcaactg gaccacattt caatcctgct ggcaaagagc atgggtctcc tgaagatgag   180
actcgtcatg ctggtgatct tggaaatatc actgttgggg atgacggaac tgcttgcttc   240
acaattgttg acaaacagat tcctctcact ggaccacact ctatcattgg tagggctgtt   300
gttgtccatg cagatcctga tgaccttggc a                                  331
```

<210> SEQ ID NO 46
<211> LENGTH: 331
<212> TYPE: DNA
<213> ORGANISM: Betula pendula

<400> SEQUENCE: 46

```
actatccact ttacccaaga agctgatggc ccaactacag taactggaaa tatttctggc    60
cttaagcctg gctccatgg gttccatgtc catgcacttg ggacacaac aaatggttgc    120 atgtcaactg ggccacattt caatcctgct ggcaaagagc atggtgctcc tgaggatgag   180
aatcgtcatg ccggtgatct gggaaatgtc accgttggtg atgatggtac tgccagtttc   240
acaatagttg acaagcagat tccactttct ggaccacatt ctattattgg aagggctgtt   300
gttgtccacg gggatccaga tgatcttggc a                                  331
```

<210> SEQ ID NO 47

<210> SEQ ID NO 47
<211> LENGTH: 390
<212> TYPE: DNA
<213> ORGANISM: Potentilla atrosanguinea

<400> SEQUENCE: 47

| | | |
|---|---|---|
| ctttacccaa gagggagatg gcccaactac tgtgaccgga acatttctg gcctcaagcc | 60 |
| tgggcttcat ggtttccatg ttcatgctct tggggacaca accaatggtt gcatgtcaac | 120 |
| tggaccacat ttcaatcctg ctggcaaaga gcatgggtct cctgaagatg agactcgtca | 180 |
| tgctggtgat cttggaaata tcactgttgg ggatgacgga actgcttgct tcacaattgt | 240 |
| tgacaaacag attcctctca ctggaccaca ctctatcatt ggtagggctg ttgttgtcca | 300 |
| tgcagatcct gatgaccttg gcaagggtgg acatgagctt agcaaatcca ctggaaatgc | 360 |
| tggtggcagg atagcttgtg gtattattgg | 390 |

<210> SEQ ID NO 48
<211> LENGTH: 390
<212> TYPE: DNA
<213> ORGANISM: Populus tremula x Populus tremuloides

<400> SEQUENCE: 48

| | | |
|---|---|---|
| ctttacccaa gaaggagatg gtccaactac tgtaactgga agcctctgtg gtcttaagcc | 60 |
| aggccttcat ggcttccatg ttcatgccct tggagacacc acaaatggct gcatgtcaac | 120 |
| tggcccgcat tttaatcctg taggcaaaga gcatggtgcc cctgaggatg agaatcgtca | 180 |
| tgctggtgat ttgggaaatg tcactgttgg tgatgatggc accgctactg tctcaatcat | 240 |
| tgacaaccag attcctctca ctggaccaaa ttccatcgtt ggaagggctg ttgttgttca | 300 |
| tgcagatcct gatgatcttg gcaagggagg acatgaactt agcaaaagca ctggtaatgc | 360 |
| tggtggcaga gtagcatgtg gtgttattgg | 390 |

<210> SEQ ID NO 49
<211> LENGTH: 446
<212> TYPE: DNA
<213> ORGANISM: Potentilla atrosanguinea

<400> SEQUENCE: 49

| | | |
|---|---|---|
| aagggcgttg ctgtacttag ctccagtgag ggtgttgctg gaactatcct ctttacccaa | 60 |
| gagggagatg gcccaactac tgtgaccgga acatttctg gcctcaagcc tgggcttcat | 120 |
| ggtttccatg ttcatgctct tggggacaca accaatggtt gcatgtcaac tggaccacat | 180 |
| ttcaatcctg ctggcaaaga gcatgggtct cctgaagatg agactcgtca tgctggtgat | 240 |
| cttggaaata tcactgttgg ggatgacgga actgcttgct tcacaattgt tgacaaacag | 300 |
| attcctctca ctggaccaca ctctatcatt ggtagggctg ttgttgtcca tgcagatcct | 360 |
| gatgaccttg gcaagggtgg acatgagctt agcaaatcca ctggaaatgc tggtggcagg | 420 |
| atagcttgtg gtattattgg ccttca | 446 |

<210> SEQ ID NO 50
<211> LENGTH: 446
<212> TYPE: DNA
<213> ORGANISM: Plantago major

<400> SEQUENCE: 50

| | | |
|---|---|---|
| aagggtgttg cagtgcttag cagcagtgag ggtgttagtg gcaccgtcct cttttcccaa | 60 |
| gaaggagaag gacccaccac tgtaactgga aacctttctg gccttaagcc tggacttcac | 120 |
| ggcttccatg ttcatgctct tggtgacact accaacggtt gcatgtcaac aggaccacat | 180 |

```
ttcaatccgg ctgcaaaaga gcatggtgct cctgatgatg aggttcgcca tgctggtgac      240
cttggtaatg tcacagtggg agatgatgga actgcaagtt tcaccattgt tgacaagctg      300
attccgctga ctggaccaca ttccatcatt ggaagggctg ttgttgtcca tgctgacccc      360
gatgatttgg aaggggtgg acatgaactc agcaaaacta ccggaaatgc tggtggaaga       420
gttgcttgtg gtatcattgg tcttca                                            446

<210> SEQ ID NO 51
<211> LENGTH: 401
<212> TYPE: DNA
<213> ORGANISM: Potentilla atrosanguinea

<400> SEQUENCE: 51
ggaactatcc tctttaccca agagggagat ggcccaacta ctgtgaccgg aaacatttct       60
ggcctcaagc ctgggcttca tggtttccat gttcatgctc ttggggacac aaccaatggt      120
tgcatgtcaa ctggaccaca tttcaatcct gctggcaaag agcatgggtc tcctgaagat      180
gagactcgtc atgctggtga tcttggaaat atcactgttg ggatgacgg aactgcttgc       240 ttcacaattg ttgacaaaca gattcctctc actggaccac actctatcat tggtagggct      300
gttgttgtcc atgcagatcc tgatgacctt gcaagggtg acatgagct agcaaatcc         360 actggaaatg ctggtggcag atagcttgt ggtattattg g                           401

<210> SEQ ID NO 52
<211> LENGTH: 401
<212> TYPE: DNA
<213> ORGANISM: Manihot esculenta

<400> SEQUENCE: 52
ggaacaatct tctttaccca agaaggagat ggtcctacca ctgtaactgg aaacatttcc      60
ggccttaagc cagggcttca tgggttccac gtccatgccc ttggagacac aacaaacggt     120
tgcatgtcaa ctgggccaca ctttaaccct tctggcaaag atcatggtgc ccctgaggat     180
gagattcgtc atgctggtga tctgggaaat gtcactgctg gtgatgatgg cactgctagt     240
ttcacaatta ttgacaagca tattcctctt tctggtcaaa attcaatcat aggaagggca     300
gttgttgttc atgcagatcc tgatgatctt ggcaggggag gacatgaact cagtaaaacc     360
accggaaatg ctggtggcag agtagcatgc ggtattattg g                          401

<210> SEQ ID NO 53
<211> LENGTH: 398
<212> TYPE: DNA
<213> ORGANISM: Potentilla atrosanguinea

<400> SEQUENCE: 53
tttacccaag agggagatgg cccaactact gtgaccggaa acatttctgg cctcaagcct      60
gggcttcatg gtttccatgt tcatgctctt ggggacacaa ccaatggttg catgtcaact     120
ggaccacatt tcaatcctgc tggcaaagag catgggtctc ctgaagatga gactcgtcat     180
gctggtgatc ttggaaatat cactgttggg atgacggaa ctgcttgctt cacaattgtt     240
gacaaacaga ttcctctcac tggaccacac tctatcattg gtagggctgt tgttgtccat     300
gcagatcctg atgaccttgg caagggtgga catgagctta gcaaatccac tggaaatgct     360
ggtggcagga tagcttgtgg tattattggc cttcaagg                              398

<210> SEQ ID NO 54
```

<210> SEQ ID NO 54
<211> LENGTH: 398
<212> TYPE: DNA
<213> ORGANISM: Condonopsis lanceolata

<400> SEQUENCE: 54

```
tttacccaag agggagatgg cccaactaaa gttactggaa gcctttctgg ccttcaacct      60
ggacctcacg gtttccatgt tcatgccctt ggtgacacaa ccaatggttg catgtcaact     120
ggtcctcatt ataatcctgc tggaaaagaa catggtgctc cagaggacga gattcgtcat     180
gctggtgacc tcgggaatgt tacagtaggc gaagacggta ctgcaaattt caccatcgtt     240
gacaaccaga ttccactatc tggacctcat tctatcattg gaagggctgt agttgtccat     300
gctgatcctg atgatcttgg aaagggtggc catgaactca gcaaaagcac tggaaatgct     360
ggtggcagga ttgcctgtgg tatcattgga ctgcaagg                             398
```

<210> SEQ ID NO 55
<211> LENGTH: 394
<212> TYPE: DNA
<213> ORGANISM: Potentilla atrosanguinea

<400> SEQUENCE: 55

```
cccaagaggg agatggccca actactgtga ccggaaacat ttctggcctc aagcctgggc      60
ttcatggttt ccatgttcat gctcttgggg acacaaccaa tggttgcatg tcaactggac     120
cacatttcaa tcctgctggc aaagagcatg gtctcctga agatgagact cgtcatgctg     180
gtgatcttgg aaatatcact gttggggatg acggaactgc ttgcttcaca attgttgaca     240
aacagattcc tctcactgga ccacactcta tcattggtag ggctgttgtt gtccatgcag     300
atcctgatga ccttggcaag ggtggacatg agcttagcaa atccactgga aatgctggtg     360
gcaggatagc ttgtggtatt attggccttc aagg                                 394
```

<210> SEQ ID NO 56
<211> LENGTH: 394
<212> TYPE: DNA
<213> ORGANISM: Gossypium hirsutum
<220> FEATURE:
<221> NAME/KEY: modified_base
<222> LOCATION: (158)
<223> OTHER INFORMATION: a, c, g, t, unknown or other
<220> FEATURE:
<221> NAME/KEY: modified_base
<222> LOCATION: (191)
<223> OTHER INFORMATION: a, c, g, t, unknown or other
<220> FEATURE:
<221> NAME/KEY: modified_base
<222> LOCATION: (221)
<223> OTHER INFORMATION: a, c, g, t, unknown or other
<220> FEATURE:
<221> NAME/KEY: modified_base
<222> LOCATION: (251)
<223> OTHER INFORMATION: a, c, g, t, unknown or other

<400> SEQUENCE: 56

```
cccaagaagg agatggtcca actaccgtga ctgggaacct ttctggtctt aagccgggac      60
tccatggctt ccatgttcat gcccttgggg acacaactaa cggtgcatg tcaactggac     120
cccattttaa tcctgctggc aaagagcatg gtgctccnga agatgagaac cgccatgctg     180
gtgatctagg naatgtcact gttggtgatg atggctgtgc nagcttctcc atcaccgaca     240
aacagattcc nctcacaggc ccaaactcca ttatcggaag agctgtagtt gtccatgcag     300
atcccgatga ccttggcaag ggcggccatg agctcagcaa aagcacagga aatgctggcg     360
gcagagtagc ttgcggtatt attggtctgc aagg                                 394
```

<210> SEQ ID NO 57
<211> LENGTH: 331
<212> TYPE: DNA
<213> ORGANISM: Potentilla atrosanguinea

<400> SEQUENCE: 57

```
ctttacccaa gagggagatg gcccaactac tgtgaccgga aacatttctg gcctcaagcc      60
tgggcttcat ggtttccatg ttcatgctct tggggacaca accaatggtt gcatgtcaac     120
tggaccacat ttcaatcctg ctggcaaaga gcatgggtct cctgaagatg agactcgtca     180
tgctggtgat cttggaaata tcactgttgg ggatgacgga actgcttgct tcacaattgt     240
tgacaaacag attcctctca ctggaccaca ctctatcatt ggtagggctg ttgttgtcca     300
tgcagatcct gatgaccttg gcaagggtgg a                                    331
```

<210> SEQ ID NO 58
<211> LENGTH: 331
<212> TYPE: DNA
<213> ORGANISM: Fagus sylvatica

<400> SEQUENCE: 58

```
ctttgcccaa gaaggagatg gcccaactac agtaactgga aatatttctg gccttaaacc      60
tggactccat ggcttccacg tgcatgctct tggggacaca acaaatggtt gcatgtcaac     120
tggaccacat ttcaatcctg ctggcaaagg gcatggtgct cctgaggatg cgaatcgtca     180
tgctggtgat ctgggaaatg tcaatgttgg tgatgatggc acagtcagtt tcacaataat     240
tgacaaacag attccacttt gtggtccaaa ttccattatc ggaagggctg ttgttgtcca     300
tggagatcca gatgatcttg gcaagggtgg a                                    331
```

<210> SEQ ID NO 59
<211> LENGTH: 399
<212> TYPE: DNA
<213> ORGANISM: Potentilla atrosanguinea

<400> SEQUENCE: 59

```
ctttacccaa gagggagatg gcccaactac tgtgaccgga aacatttctg gcctcaagcc      60
tgggcttcat ggtttccatg ttcatgctct tggggacaca accaatggtt gcatgtcaac     120
tggaccacat ttcaatcctg ctggcaaaga gcatgggtct cctgaagatg agactcgtca     180
tgctggtgat cttggaaata tcactgttgg ggatgacgga actgcttgct tcacaattgt     240
tgacaaacag attcctctca ctggaccaca ctctatcatt ggtagggctg ttgttgtcca     300
tgcagatcct gatgaccttg gcaagggtgg acatagcctt agcaaatcca ctggaaatgc     360
tggtggcagg atagcttgtg gtattattgg ccttcaagg                            399
```

<210> SEQ ID NO 60
<211> LENGTH: 399
<212> TYPE: DNA
<213> ORGANISM: Citrus limon

<400> SEQUENCE: 60

```
ctttacccag gaaggagatg gtccaacaac tgtttcagga agcctctctg gtctcaagcc      60
tggtcctcat ggattccatg ttcatgctct tggagacaca acaaatggtt gcatgtctac     120
tggacccac tttaaccctg ctggaaaaga acatggagct ccagaggatg ataatcgtca     180
tgctggtgat ttaggaaatg tcaatgttag tgatgatggt actgctactt ttacagttgt     240
```

```
tgacaatcag attcctcttt ctggaccaaa ttccattatt ggaagggctg ttgtagtcca    300
cgcagatccc gatgatcttg caagggcgg tcatgagctg agcaaaacca ctggaaatgc     360
tggtggcaga gtagcttgcg gcataattgg cctccaagg                           399
```

<210> SEQ ID NO 61
<211> LENGTH: 375
<212> TYPE: DNA
<213> ORGANISM: Potentilla atrosanguinea

<400> SEQUENCE: 61

```
ccaagaggga gatggcccaa ctactgtgac cggaaacatt tctggcctca agcctgggct    60
tcatggtttc catgttcatg ctcttgggga cacaaccaat ggttgcatgt caactggacc   120
acatttcaat cctgctggca aagagcatgg gtctcctgaa gatgagactc gtcatgctgg   180
tgatcttgga aatatcactg ttggggatga cggaactgct tgcttcacaa ttgttgacaa   240
acagattcct ctcactggac cacactctat cattggtagg gctgttgttg tccatgcaga   300
tcctgatgac cttggcaagg gtggacatga gcttagcaaa tccactggaa atgctggtgg   360
caggatagct tgtgg                                                     375
```

<210> SEQ ID NO 62
<211> LENGTH: 375
<212> TYPE: DNA
<213> ORGANISM: Bruguiera gymnorhiza

<400> SEQUENCE: 62

```
ccaagaggga gatggcccaa ctactgtaac tggaaatgtt tctggcctta agtcagggct    60
tcatggcttc catgttcatg ctcttgggga cactacaaat ggttgcatgt caactgggcc   120
gcacttcaat ccaggtagca aagagcatgg tgcccctgaa gacgagaacc gtcatgccgg   180
tgacctagga aatgtaaatg ttgcggatga tggcactgca acattcacaa tcactgacaa   240
tcagattcct cttactggac ccaattccat tgttggaagg gctgttgttg ttcatgctga   300
tcctgatgat ctgggcaagg gagggcatga acttagcaaa agcactggaa atgctggtgg   360
cagggtagca tgtgg                                                     375
```

<210> SEQ ID NO 63
<211> LENGTH: 390
<212> TYPE: DNA
<213> ORGANISM: Potentilla atrosanguinea

<400> SEQUENCE: 63

```
ctttacccaa gagggagatg gcccaactac tgtgaccgga acatttctg gcctcaagcc     60 tgggcttcat ggtttccatg ttcatgctct tggggacaca accaatggtt gcatgtcaac   120
tggaccacat ttcaatcctg ctggcaaaga gcatgggtct cctgaagatg agactcgtca   180
tgctggtgat cttggaaata tcactgttgg ggatgacgga actgcttgct tcacaattgt   240
tgacaaacag attcctctca ctggaccaca ctctatcatt ggtagggctg ttgttgtcca   300
tgcagatcct gatgaccttg caagggtgg acatgagctt agcaaatcca ctggaaatgc    360
tggtggcagg atagcttgtg gtattattgg                                     390
```

<210> SEQ ID NO 64
<211> LENGTH: 390
<212> TYPE: DNA
<213> ORGANISM: Populus alba

<400> SEQUENCE: 64

-continued

```
ctttacccaa gaaggagatg gtccaactac tgtaactgga agcctctgtg gtcttaagcc    60
aggccttcat ggcttccatg ttcatgccct tggagacacc acaaatggct gcatgtcaac   120
tggcccgcat tttaatcctg taggcaaaga gcatggtgcc cctgaggatg agaatcgtca   180
tgctggtgat ttgggaaatg tcactgttgg tgatgatggc accgctactg tctcaatcat   240
tgacaaccag attcctctta ctggaccaaa ttccattgtt ggaagggcag ttgttgttca   300
tgcagatcct gatgatcttg caagggagg acatgaactt agcaaaagca ctggtaatgc    360
tggtggcaga gtagcatgtg gtgttattgg                                     390
```

<210> SEQ ID NO 65
<211> LENGTH: 390
<212> TYPE: DNA
<213> ORGANISM: Potentilla atrosanguinea

<400> SEQUENCE: 65

```
ctttacccaa gagggagatg gcccaactac tgtgaccgga aacatttctg gcctcaagcc    60
tgggcttcat ggtttccatg ttcatgctct tggggacaca accatggttt gcatgtcaac   120
tggaccacat ttcaatcctg ctggcaaaga gcatgggtct cctgaagatg agactcgtca   180
tgctggtgat cttggaaata tcactgttgg ggatgacgga actgcttgct tcacaattgt   240
tgacaaacag attcctctca ctggaccaca ctctatcatt ggtagggctg ttgttgtcca   300
tgcagatcct gatgaccttg caagggtgg acatgagctt agcaaatcca ctggaaatgc    360
tggtggcagg atagcttgtg gtattattgg                                     390
```

<210> SEQ ID NO 66
<211> LENGTH: 390
<212> TYPE: DNA
<213> ORGANISM: Potentilla atrosanguinea

<400> SEQUENCE: 66

```
ctttacccaa gaaggagatg gtccaactac tgtaactgga agcctctgtg gtcttaagcc    60
aggccttcat ggcttccatg ttcatgccct tggagacacc acaaatggct gcatgtcaac   120
tggcccgcat tttaatcctg taggcaaaga gcatggtgcc cctgaggatg agaatcgtca   180
tgctggtgat ttgggaaatg tcactgttgg tgatgatggc accgctactg tctcaatcat   240
tgacaaccag attcctctta ctggaccaaa ttccattgtt ggaagggcag ttgttgttca   300
tgcagatcct gatgatcttg caagggagg acatgaactt agcaaaagca ctggtaatgc    360
tggtggcaga gtagcatgtg gtgttattgg                                     390
```

<210> SEQ ID NO 67
<211> LENGTH: 423
<212> TYPE: DNA
<213> ORGANISM: Potentilla atrosanguinea

<400> SEQUENCE: 67

```
cagtgagggt gttgctggaa ctatcctctt tacccaagag ggagatggcc caactactgt    60
gaccggaaac atttctggcc tcaagcctgg gcttcatggt ttccatgttc atgctcttgg   120
ggacacaacc aatggttgca gtcaactgg accacatttc aatcctgctg gcaaagagca    180
tgggtctcct gaagatgaga ctcgtcatgc tggtgatctt ggaaatatca ctgttgggga   240
tgacggaact gcttgcttca caattgttga caaacagatt cctctcactg gaccacactc   300
tatcattggt agggctgttg ttgtccatgc agatcctgat gaccttggca agggtggaca   360
```

-continued tgagcttagc aaatccactg gaaatgctgg tggcaggata gcttgtggta ttattggcct    420
tca                                                                 423

<210> SEQ ID NO 68
<211> LENGTH: 423
<212> TYPE: DNA
<213> ORGANISM: Populus alba

<400> SEQUENCE: 68
cagtgagggt gttagtggca ccatctactt cacccaggaa ggagatggtc caacaactgt    60
tactggaaac gtttctggcc ttaagcctgg accccatggc tttcatgtgc atgcccttgg   120
tgacaccacc aatggttgtt tgtcaactgg acctcacttc aatcctgctg caaagagca    180 tggagctcct gatgatgagg ttcgccatgc tggtgacctt gggaatgtca cagttggaga   240
agatggcact gctgctttca ctattgttga caagcagata ccacttacag gaccacattc    300
cataattgga agagctgtag ttgttcatgc tgatcctgat gatcttggaa agggtggaca   360
tgaactgagc aaaaccactg gaaatactgg tggaagagtt gcttgtggta tcaatggcct    420
tca                                                                 423

<210> SEQ ID NO 69
<211> LENGTH: 392
<212> TYPE: DNA
<213> ORGANISM: Potentilla atrosanguinea

<400> SEQUENCE: 69
acccaagagg gagatggccc aactactgtg accggaaaca tttctggcct caagcctggg    60
cttcatggtt tccatgttca tgctcttggg gacacaacca atggttgcat gtcaactgga   120
ccacatttca atcctgctgg caaagagcat gggtctcctg aagatgagac tcgtcatgct   180
ggtgatcttg gaaatatcac tgttggggat gacggaactg cttgcttcac aattgttgac   240
aaacagattc ctctcactgg accacactct atcattggta gggctgttgt tgtccatgca    300
gatcctgatg accttggcaa gggtggacat gagcttagca aatccactgg aaatgctggt   360
ggcaggatag cttgtggtat tattggcctt ca                                  392

<210> SEQ ID NO 70
<211> LENGTH: 392
<212> TYPE: DNA
<213> ORGANISM: Olea europaea

<400> SEQUENCE: 70
acccaagaag gagatggtcc aactactgtt actggaaacc tttctggcct taagcctgga    60
cttcatggct ttcatgtcca cgcccttggt gacaccacca atggctgtat gtcaactgga   120
cctcatttca atcctgttgg gaaagagcat ggtgcacctg agatgagaa ccgtcatgct    180 ggtgatcttg gtaatatcac agttggcgaa gatggcaccg ctgctatcaa cattgttgac   240
aagcagatac ctcttacagg accacattcc ataattggaa gagcagtagt tgtccattca    300
gatcctgatg atcttggaag gggtggtcat gaactgagca agagcactgg aaatgctggt   360
ggaagagttg cttgtggtat cattggcctt ca                                  392

<210> SEQ ID NO 71
<211> LENGTH: 395
<212> TYPE: DNA
<213> ORGANISM: Potentilla atrosanguinea

<400> SEQUENCE: 71

```
atcctcttta cccaagaggg agatggccca actactgtga ccggaaacat ttctggcctc      60
aagcctgggc ttcatggttt ccatgttcat gctcttgggg acacaaccaa tggttgcatg     120
tcaactggac cacatttcaa tcctgctggc aaagagcatg ggtctcctga agatgagact     180
cgtcatgctg gtgatcttgg aaatatcact gttggggatg acggaactgc ttgcttcaca     240
attgttgaca aacagattcc tctcactgga ccacactcta tcattggtag ggctgttgtt     300
gtccatgcag atcctgatga ccttggcaag ggtggacatg agcttagcaa atccactgga     360
aatgctggtg gcaggatagc ttgtggtatt attgg                                395

<210> SEQ ID NO 72
<211> LENGTH: 395
<212> TYPE: DNA
<213> ORGANISM: Solanum tuberosum

<400> SEQUENCE: 72
atcctcttca ctcaagatgg agatgctcca accacagtta atggaaatat ttctggccta      60
aaacctggac ttcatggctt ccatgtccat gcccttggtg ataccacaaa tggctgcatg     120
tcaacaggac cacattacaa tcctgctggt aaggagcatg gtgctcctga agatgaggtg     180
cgtcatgctg gtgatcttgg taacatcaca gttggagaag atggtactgc atctttact     240 attaccgaca agcagattcc tctcactggt tcacaatcca tcattggaag agctgttgtt     300
gttcatgctg atcctgatga tcttggaaag ggaggacatg agctcagtaa agcactgga     360 aatgctggcg gaaggattgc ttgtggtatt attgg                                395

<210> SEQ ID NO 73
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (56)..(57)
<223> OTHER INFORMATION: a, c, g, t, unknown or other

<400> SEQUENCE: 73
aagcagtggt atcaacgcag agtactttt ttttttttt ttttttttt tttttnn        57
```

We claim:

1. An isolated Superoxide dismutase (SOD) cDNA of SEQ ID No. 2 obtained from *Potentilla atrosanguinea*, wherein said cDNA comprises 856 nucleotide bases.

2. The Superoxide dismutase (SOD) cDNA as claimed in claim 1, wherein said cDNA has the entire coding sequence along with pre- and post-coding sequences.

3. An isolated Superoxide dismutase (SOD) gene of SEQ ID No. 3, wherein said gene comprises 459 nucleotide bases.

4. An isolated set of primers useful for the amplification of a Superoxide dismutase (SOD) gene of SEQ ID No. 3, wherein said Forward primer comprises 5'-ATG-GCAAAGGGCGTTGCTGTACTT-3' (SEQ ID NO: 5) and;

said Reverse primer comprises 5'-TCATCCTTGAAGGC-CAATAATACCA-3' (SEQ ID NO: 6).

5. An expression construct comprising a nucleotide sequence of a superoxide dismutase (SOD) gene of SEQ ID NO 3 which codes for a polypeptide of SEQ ID No. 1 having Superoxide dismutase enzyme activity, a selectable marker and a terminator sequence.

* * * * *